United States Patent
Ziady et al.

(10) Patent No.: US 10,761,099 B2
(45) Date of Patent: Sep. 1, 2020

(54) COMPOSITIONS AND METHODS FOR TREATMENT OF LUNG FUNCTION

(71) Applicant: Children's Hospital Medical Center, Cincinnati, OH (US)

(72) Inventors: Assem Ziady, Newport, KY (US); Rhonda Szczesniak, Burlington, KY (US); John Clancy, Cincinnati, OH (US); Cole Brokamp, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/927,575

(22) Filed: Mar. 21, 2018

(65) Prior Publication Data

US 2018/0275141 A1    Sep. 27, 2018

Related U.S. Application Data

(60) Provisional application No. 62/474,739, filed on Mar. 22, 2017.

(51) Int. Cl.
*G01N 33/68* (2006.01)
*G01N 33/53* (2006.01)

(52) U.S. Cl.
CPC ..... *G01N 33/6893* (2013.01); *G01N 33/6851* (2013.01); *G01N 2333/914* (2013.01); *G01N 2800/382* (2013.01); *G01N 2800/50* (2013.01); *G01N 2800/56* (2013.01)

(58) Field of Classification Search
None
See application file for complete search history.

(56) References Cited

U.S. PATENT DOCUMENTS 4,208,479 A * 6/1980 Zuk .................. C07J 41/0016
435/7.72

OTHER PUBLICATIONS

Kormelink et al. (PLOs 2011 6: e25392). (Year: 2011).*
Peila et al. (Italian Journal of Pediatrics 2016 42:36 total 8 pages) (Year: 2016).*
Chronny et al. (Journal Proteome Research 2004 vol. 3, p. 1120-1127) (Year: 2004).*
Accurso FJ, et al., "Effect of VX-770 in Persons with Cystic Fibrosis and the G551D-CFTR Mutation." N Engl J Med, Nov. 18, 2010, 363(21):1991-2003, 13 pgs.
Albert PS, et al., "An Approach for Jointly Modeling Multivariate Longitudinal Measurements and Discrete Time-To-Event Data," Ann Appl Stat, 2010, 4(3):1517-1532, 16 pgs.
Asar O, et al., "mmm: An R package for analyzing multivariate longitudinal data with multivariate marginal models," Comput Methods Programs Biomed, 2013, 112(3):649-654, 6 pgs.
Brebner JA, et al., "Polyclonal free light chains: a biomarker of inflammatory disease or treatment target?" F1000 Med Rep, 2013, 5:4, 6 pgs.
Chatterjee N, et al., "Constrained Maximum Likelihood Estimation for Model Calibration Using Summary-level Information from External Big Data Sourcesm" J Am Stat Assoc, 2016, 111(513):107-117, 11 pgs.
Chen J, et al., "Dysfunction of Nrf-2 in CF Epithelia Leads to Excess Intracellular $H_2O_2$ and Inflammatory Cytokine Production," PLoS One, 2008, 3(10):e3367, 12 pgs.
Chen X, et al., "Nucleolin-Mediated Cellular Trafficking of DNA Nanoparticle Is Lipid Raft and Microtubule Dependent and Can Be Modulated by Glucocorticoid," Mol Ther, 2011, 19(1):93-102, 10 pgs.
Chipman HA, et al., "BART: Bayesian Additive Regression Trees," Ann Appl Stat, 2014, 23(1):42-59, 33 pgs.
Chirkova T, et al., "CX3CR1 is an important surface molecule for respiratory syncytial virus infection in human airway epithelial cells," J Gen Virol, 2015, 96:2543-2556, 14 pgs.
Chmiel J, et al., "The Effect of Sulforaphane in Broccoli Sprouts on Nrf2 Activation, Glutathione, Markers of Oxidative Stress, and Neutrophil Migration," Pediatr Pulmonol, 2012, 47(S35):250; 2012 Cystic Fibrosis Conference, Poster Session Abstract 82*, 1 pg.
Clancy JP, et al., "Personalized Medicine in Cystic Fibrosis: Dawning of a New Era," Am J Respir Crit Care Med, 2012, 186(7):593-597, 5 pgs.
Diggle PJ, et al., "Real-time monitoring of progression towards renal failure in primary care patients," Biostatistics, 2015, 16(3):522-536, 15 pgs.
Drumm ML, et al., "Genetic Variation and Clinical Heterogeneity in Cystic Fibrosis," Annu Rev Pathol, 2012, 7:267-282, 18 pgs.
Duan LL, et at., "Bayesian Ensemble Trees (BET) for Clustering and Prediction in Heterogeneous Data," J Comput Graph Stat, 2016, 25(3):748-761, 14 pgs.
Duan LL, et al., "Joint Hierarchical Gaussian Process Model with Application to Forecast in Medical Monitoring," 2014, eprint arXiv:1408.4660, 23 pgs.
Fieuws S, et al., "Predicting renal graft failure using multivariate longitudinal profiles," Biostatistics, 2008, 9(3):419-431, 13 pgs.
Fieuws S, et al., "Random-effects models for multivariate repeated measures," Stat Methods Med Res, Oct. 2007, 16(5):387-397, 11 pgs.
Fischer K, et al., "Biomarker Profiling by Nuclear Magnetic Resonance Spectroscopy for the Prediction of All-Cause Mortality: An Observational Study of 17,345 Persons," PLoS Med, Feb. 2014, 11(2):e1001606, 12 pgs.

(Continued)

*Primary Examiner* — Changhwa J Cheu
(74) *Attorney, Agent, or Firm* — Frost Brown Todd LLC; Nicole M. Tepe

(57) ABSTRACT

Disclosed herein are methods for detecting protein expression in an individual diagnosed with cystic fibrosis. The methods, in certain aspects, include the steps of obtaining a sample from said individual and detecting expression in said sample of each protein of a protein set. The method may further include the step of determining expression level of one or more proteins of the protein set. The disclosed methods may be used to predict one or more clinical parameters in an individual having cystic fibrosis.

15 Claims, 11 Drawing Sheets

(56) References Cited

OTHER PUBLICATIONS

Harun SN, et al., "A systematic review of studies examining the rate of lung function decline in patients with cystic fibrosis," Paediatr Respir Rev, 2016, 20:55-66, 12 pgs.
Hastie T, et al., *The Elements of Statistical Learning: Data Mining, Inference, and Prediction*, Second Ed, Springer Science + Busness Media, LLC, New York, NY, 2009, (Table of Contents Only) 12 pgs.
James GM, et al., "Principal component models for sparse functional data," Biometrika, 2000, 87(3):587-602, 16 pgs.
Jiang C-R, et al., "Covariate Adjusted Functional Principal Components Analysis For Longitudinal Data," The Annals of Statistics, 2010, 38(2): 1194-1226, 24 pages.
Kim PY, et al., "Identification of plasma Complement C3 as a potential biomarker for neuroblastoma using a quantitative proteomic approach," J Proteomics, 2014, 96: 1-12, 12 pgs.
La Rosa PS, et al., "Hypothesis Testing and Power Calculations for Taxonomic-Based Human Microbiome Data," PLoS One, 2012, 7(12):e52078, 13 pgs.
Laguna TA, et al., "Sputum Desmosine DuIing Hospital Admission for Pulmonary Exaceibation in Cystic Fibrosis," Chest, Dec. 2009, 136(6): 1561-1568, 8 pgs.
Lancioni CL, et al., "*Mycobacterium tuberculosis* Lipoproteins Directly Regulate Human Memory CD4+ T Cell Activation via Toll-Like Receptors 1 and 2," Infect Immun, Feb. 2011, 79(2):663-673, 11 pgs.
Li Q, et al., "Rv2468c, a Novel *Mycobacterium tuberculosis* protein that costimulates human $CD4^+$ T cells through VLA-5," J Leukoc Biol, Feb. 2012, 91(2):311-20, 10 pgs.
Liou TG, et al., "Year-to-year changes in lung function in individuals with cystic fibrosis," J Cyst Fibros, 2010, 9(4):250-6, 7 pgs.
Nick JA, et al., "Blood mRNA biomarkers for detection of treatment response in acute pulmonary exacerbations of cystic fibrosis," Thorax, 2013, 68(10):929-937, 9 pgs.
Obuchowski NA, et al., "Sample Size Determination for Diagnostic Accuracy Studies Involving Binormal ROC Curve Indices," Stat Med, 1997, 16(13):1529-1542, 14 pgs.
Ramsay JO, et al., *Functional data analysis*, Second Ed., Springer Science + Business Media, Inc., New York., NY, 2005, p. 426, (Table of Contents only) 13 pgs.
Ratjen F, et al., "Effect of Azithromycin on Systemic Markers of Inflammation in Patients With Cystic Fibrosis Uninfected With *Pseudomonas aeruginosa*," Chest, 2012, 142(5):1259-1266, 8 pgs.
Rosenfeld M, et al., "Baseline Characteristics and Factors Associated With Nutritional and Pulmonary Status at Enrollment in the Cystic Fibrosis EPIC Observational Cohort," Pediatr Pulmonol, 2010, 45(9):934-944, 11 pgs.
Rosenfeld M, et al., "Decline in Lung Function Does not Predict Future Decline in Lung Function in Cystic Fibrosis Patients," Pediatr Pulmonol, 2015, 50(9):856-862, 7 pgs.
Sagel SD, et al., "Effect of Treatment of Cystic Fibrosis Pulmonary Exacerbations on Systemic Inflammation," Ann Am Thorac Soc, 2015, 12(5):708-717, 10 pgs.
Sagel SD, et al., "Validation of Candidate Serum Protein and Lipid Markers of Disease Severity in CF," Pediatr Pulmonol, 2014, 49(S38):288, 2014 Cystic Fibrosis Conference, Poster Session Abstract 205*, 1 pg.
Sanders DB, et al., "Failure to Recover to Baseline Pulmonary Function after Cystic Fibrosis Pulmonary Exacerbation," Am J Respir Crit Care Med, 2010, 182(5):627-32, 6 pgs.
Schluchter MD, et al., "Classifying Severity of Cystic Fibrosis Lung Disease Using Longitudinal Pulmonary Function Data," Am J Respir Crit Care Med, 2006, 174(7):780-786, 7 pgs.
Sinha C, et al., "PKA and actin play critical roles as downstream effectors in MRP4-mediated regulation of fibroblast migration," Cell Signal, 2015, 27(7):1345-1355, 11 pgs.
Sinha C, et al., "Capturing the Direct Binding of CFTR Correctors to CFTR by Using Click Chemistry," Chembiochem, 2015, 16:2017-2022, 6 pgs.
Slobodianik NH, et al., "Inflammatory biomarker profile in children with cystic fibrosis: preliminary study," Proc Nutr Soc, $3^{rd}$ International Immunonutrition Workshop; Session 4: Dietary strategies to preent and mitigate inflammaroty diseases, 2010, 69(3):354-356, 3 pgs.
Szczesniak RD, et al., "A semiparametric approach to estimate rapid lung function decline in cystic fibrosis," Annals of Epidemiology, 2013, 23(12):771-777, 7 pgs.
Szczesniak RD, et al., "Phenotypes of Rapid Cystic Fibrosis Lung Disease Progression during Adolescence and Young Adulthood," American Journal of Respiratory and Critical Care Medicine, 2017, 196(4): 471-478, 8 pgs.
Szczesniak RD, et al., "Predicting Future Lung Function Decline in Cystic Fibrosis Patients: Statistical Methods and Clinical Connections," Pediatr Pulmonol, Letter to the Editor, 2016, 51(2):217-218, 2 pgs.
Tang Y, et al., "Developing Adaptive Personalized Therapy for Cystic Fibrosis Using Reinforcement Learning," Submitted to Ann Appl Stat, 2012, 28 pgs.
Taylor-Robinson D, et al., "Understanding the natural progression in $%FEV_1$ decline in patients with cystic fibrosis: a longitudinal study," Thorax, 2012, 67(10):860-866, 7 pgs.
Tibshirani RJ., "Regression Shrinkage and Selection via the Lasso," J R Statist Soc B, 1996, 58(1):267-288, 22 pgs.
Tucholska M, et al., "Human Serum Proteins Fractionated by Preparative Partition Chromatography Prior to LC-ESI-MS/MS," J Proteome Res, 2009, 8(3):1143-1155, 13 pgs.
Verbeke G, et al., "The analysis of multivariate longitudinal data: A review," Stat Methods Med Res, 2014, 23(1):42-59, 18 pgs.
Wainwright CE, et al., "Lumacaftor-Ivacaftor in Patients with Cystic Fibrosis Homozygous for Phe508del CFTR," N Engl J Med, 2015, 373(3):220-231, 12 pgs.
Wang J, et al., "Measuring the impact of apnea and obesity on circadian activity patterns using functional linear modeling of actigraphy data," J Circadian Rhythyms, 2011, 9(1):11, 10 pgs.
Wang X, et al., "Hsp90 Cochaperone Aha1 Downregulation Rescues Misfolding of CFTR in Cystic Fibrosis," Cell, 2006, 127(4):803-815, 13 pgs.
Yanagisawa K, et al., "Proteomic patterns of tumour subsets in non-small-cell-lung cancer," Lancet, 2003, 362(9382):433-439, 7 pgs.
Yao, F., et al., "Functional Data Analysis for Sparse Longitudinal Data," Journal of the American Statistical Association, 2005, 100(470):577-590, 14 pgs.
Zeitzer JM, et al., "Phenotyping Apathy in Individuals With Alzheimer Disease Using Functional Principal Component Analysis," Am J Geriatr Psychiatry, 2013, 21(4):391-397, 12 pgs.
Zemanick ET, et al., "Inflammation and Airway Microbiota During Cystic Fibrosis Pulmonary Exacerbations," PLoS One, 2013, 8(4):e62917, 13 pgs.
Ziady AG, et al., "Proteomic Analyses of Serum From CF Patients With Mild or Severe Disease Reveal the Differential Expression of Proteins That Regulate the Differentiation of Cartilage, Myeloid Leukocytes, and Intestinal Epithelia" Pediatr Pulmonol, 2014, 49(S38):288, 2014 Cystic Fibrosis Conference, Poster Session Abstract 206*, 1 pg.
Ziady AG, et al., "Protein Sequencing with Tandem Mass Spectrometry," Chapter 21, James Weifu Lee, et al., Eds. *Micro and Nano Technologies in Bioanalysis*, Methods and Mol Biol, 2009, 544:325-341, 17 pgs.
Ziady AG, et al., "Proteomic Analyses of BALF Reveal Potential Biomarkers and Suggest Altered Lipid, Cyclic Nucleotide, and Iron Metabolism in Young CF Children Versus Disease Controls," Pediatr Pulmonol, 2013, 48(S36):277-278, 2013 Cystic Fibrosis Conference, Poster Session Abstract 204*, 2 pgs.
Ziady AG, et al., "Interaction with CREB binding protein modulates the activities of Nrf2 and NF-κB in cystic fibrosis airway epithelial cells," Am J Physiol Lung Cell Mol Physiol, 2012, 302(11):L1221-L1231, 11 pgs.
U.S. Appl. No. 62/474,739, filed Mar. 22, 2017.
Chui, CK, et al., "Interpolation by Multivariate Splines," Math Comput, 1988, 51(183):203-218, 16 pgs.
Green, PJ, et al., "Nonparametric regression and generalized linear models: a roughness penalty approach," $1^{st}$ ed. London, New York: Chapman & Hall, 1994, ix, 182 p. Table of Contents Only, 8 pgs.

(56) References Cited

OTHER PUBLICATIONS

Peng, J., et al., "A Geometric Approach to Maximum Likelihood Estimation of the Functional Principal Components From Sparse Longitudinal Data," J Comput Graph Stat, 2009, 18(4):995-1015, Technical Report 2007a, 87 pgs.

Peng, J., Restricted MLE for Functional Principal Components Analysis (R package fpca) 2015. Available from: https://CRAN.R-project.org/package=fpca, 12 pgs.

* cited by examiner

COMPOSITIONS AND METHODS FOR TREATMENT OF LUNG FUNCTION

CROSS-REFERENCE TO RELATED APPLICATIONS

This application claims priority to and benefit of 62/474,739, filed Mar. 22, 2017. The contents of each are incorporated in their entirety for all purposes.

GOVERNMENT SUPPORT CLAUSE

This invention was made with government support under HL116226 and HL125954 awarded by the National Institutes of Health. The government has certain rights in the invention.

BACKGROUND

Cystic fibrosis (CF) is an autosomal recessive disorder that affects approximately 30,000 individuals in the United States. The primary defect results from mutations of the cystic fibrosis transmembrane conductance regulator gene, which codes for the CFTR chloride channel. The protein is expressed predominantly on the apical surface of epithelial cells throughout the body (although low level expression has been detected in other tissues). Over 2,000 disease causing mutations have been identified in the CFTR gene, with the majority of patients (~90%) exhibiting at least one allele with the F508del mutation. Disease causing mutations fall into 5 classifications that result in abnormal CFTR protein that is either truncated, misprocessed/mislocalized, lacking channel gating function, or malformed due to improper gene splicing. With advances in new-born and other screenings, CF is usually diagnosed at birth. Although the determinants of disease are well characterized, forecasting disease progression has been extremely difficult and as of yet unsuccessful.

Care for CF patients has advanced rapidly over the past two decades, with an increase in patient longevity and quality of life that is unprecedented. The reasons for these improvements include a number of factors. First, a robust CFF Patient Registry (CFF-PR) has collected patient data from nearly all CF patients in the US, allowing assessment of outcomes and treatment responses. Next, there have been dramatic advances in new CF therapeutics (e.g. the development of recombinant human DNase, inhaled antibiotics including dissolved and dry powder tobramycin, aztreonam, hypertonic saline, low dose azithromycin to control inflammation, FDA approval of standardized pancreatic enzyme replacement, and most recently genotype-specific CFTR modulators such as KALYDECO® (4) and ORKAMBI® (5). In tandem with these new treatments, there has been a focus on the development of CF care guidelines and standardization of care across accredited CF care centers. This has helped to 'raise all boats' in the CF care community, accompanied by center-specific data to drive local quality improvement. Finally, understanding of disease severity predictors has advanced significantly, including the importance of weight in predicting pulmonary stability, the contribution of chronic Pseudomonas and MRSA infection to pulmonary decline and mortality, and the relationship between poorly controlled diabetes and disease progression. Indeed, these advancements have increased the median survival of CF patients to 41 years (CFF-PR—2014), and nearly 50% of CF patients alive today are adults.

Accompanying the improvements in CF outcomes are a number of challenges that urgently require attention. There have been dramatic global improvements in the CF disease trajectory, but many patients have not fully benefited from the advancements described above. (FIG. 3.) Indeed, the average age of death of CF patients in a given year has remained remarkably static, with most patients dying of CF lung disease during their third decade of life (CFF-PR 2014 statistics). The burden of care also remains a significant challenge, as most adolescents and young adults need to spend approximately two hours daily dedicated to therapies that maintain health. Adherence to complex care regimens is often untenable, and this has led to the need to 'personalize' care such that patients commit to daily therapies that are most likely to benefit them individually. These commitments increase during periods of instability, and treatment of PE remains highly interruptive to daily care and negatively impacts quality of life. They also are sentinel markers of disease progression, as 25% of CF patients fail to recover lung functions following PEs. The benefits of care improvements have also challenged our capacity to monitor CF lung disease and CF manifestations in other organs. Assessing the relative benefit of new therapies in the context of relatively normal lung function (as measured by routine spirometry) is particularly challenging for CF providers. This requires the development of more sensitive tools to identify subjects most likely to benefit from various interventions and to monitor the impact of new therapies added to care plans. Finally, the conduct of clinical trials to advance CF outcomes and interventions can no longer rely on standard outcome measures such as FEVi, as excessively large and/or long clinical trials are needed to demonstrate improvements in crude measurements such as lung function. Thus, the CF field stands at a crossroads, where the benefits of the past limit the capacity to advance therapies and personalize care when relying upon standard measures of disease status.

The natural history of the disease is well studied; but disease progression is not well understood. Pulmonary decline typically begins in adolescence, but current measures tend to follow rather than predict outcomes. For example, if a marker predicted disease instability and erratic swings in lung function, established or novel interventions to prevent decline could be implemented. Several clinical measures track disease progression, including forced expiratory volume in 1 sec ($FEV_1$), body mass index (BMI) and pulmonary exacerbations (PE). Presently, intervention is driven by lagging indications of lung function decline, which is far less beneficial than intervening in at risk subpopulations before decline is manifest. Therefore, markers that predict CF disease progression are highly desirable, as they would preemptively identify those at risk of future disease progression, allowing caregivers to tailor treatments and select intervention to prevent pulmonary decline. Personalizing therapy is a critical need in CF, as broad application of all available therapies leads to a high daily treatment burden and poor adherence. These measures are lagging indicators of disease progression that result from molecular changes directly or indirectly related to CFTR dysfunction. Furthermore, current monitoring of lung function data is inadequate, and fails to utilize novel biostatistical tools to identify patients at risk for future decline.

CF care has significantly increased the life span of patients, but the disease remains highly morbid and fatal. Aggressive therapy has been shown to enhance quality of life and improve survival (20); however, it is impractical and expensive to aggressively treat all patients proactively without evidence of disease progression. Therefore, caregivers have depended on outcomes measures, most of which are lagging indicators, to guide treatment decisions. Novel outcome measures of lung function decline that are superior to presently used measures are needed for improving CF patient health and survival, and personalizing care. The disclosed methods address one or more of aforementioned needs in the art.

BRIEF SUMMARY

Disclosed herein are methods for detecting protein expression in an individual diagnosed with cystic fibrosis. The methods, in certain aspects, include the steps of obtaining a sample from said individual and detecting expression in said sample of each protein of a protein set. The method may further include the step of determining expression level of one or more proteins of the protein set. The disclosed methods may be used to predict one or more clinical parameters in an individual having cystic fibrosis.

BRIEF DESCRIPTION OF THE DRAWINGS

This application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

DETAILED DESCRIPTION

Definitions

Figure 1:
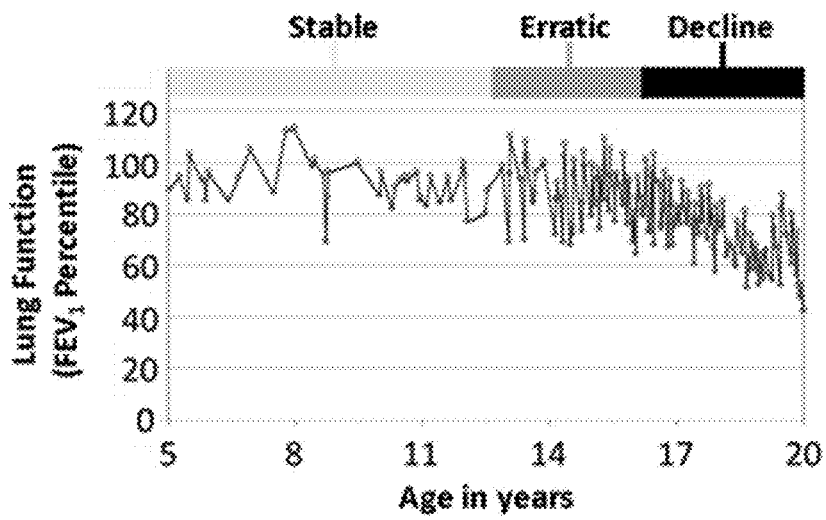
FIG. 1. Lung function in a typical CF patient. Lung is separated into stages, with a stable period (light grey), an erratic period with large swings in $FEV_1$ (dark grey), and a decline stage (black).

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

Applicant has developed a dynamic prediction model by integrating analyses of validated proteomic data with Functional Data (FD) analysis of longitudinal FEV data to produce a novel diagnostic algorithm that identifies individuals at risk of lung function decline. In another aspect, Applicant has developed dynamic prediction modeling to identify CF patients who develop rapid pulmonary decline during adolescence. Disclosed herein are methods and assays for the examination of blood protein expression and modification in longitudinal samples integrated with monitoring of FEV, changes over time through Functional Data (FD) analysis, that provide a sensitive and specific biomarker algorithm for prediction of CF lung disease progression that is superior to current practice. In particular, Applicant has found that novel serum biomarkers of disease severity enhance the ability of FD analysis to predict FEV, decline.

Figure 2:
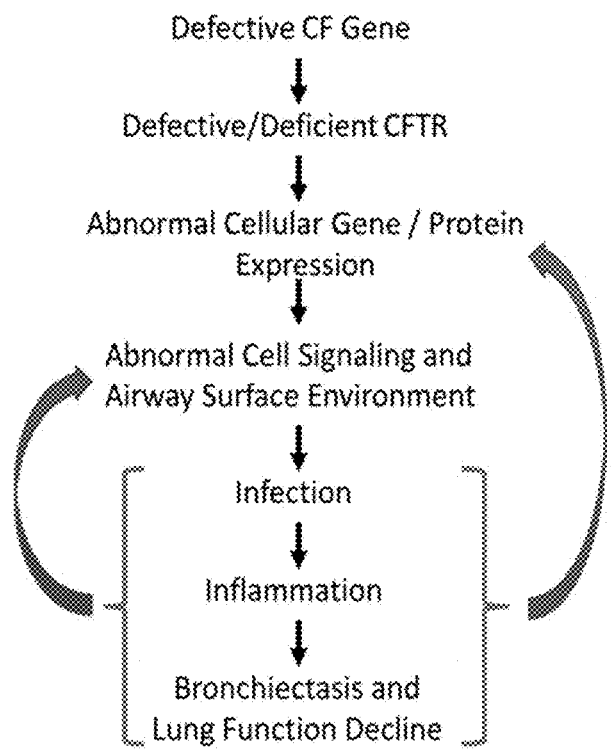
FIG. 2. Disease progression in CF. In depth serum proteomic analysis can capture molecular changes in serum that give rise to downstream organ pathology.

Three important measures are used in monitoring CF disease progression and response to therapy; $FEV_1$, PE frequency, and BMI. Although these measures, specifically of lung function ($FEV_1$), have demonstrated steady improvement over the past two decades, a rapid deterioration of lung function persists, especially during adolescence. (FIG. 2.) Although $FEV_1$, PE, and BMI are trailing indicators of disease progression, they are phenotypic culminations of molecular changes that persist and continue to influence the course of disease. In addition to the deleterious effects of CF disease progression (such as mucus plugging, bacterial infection, and inflammation), these clinical measures reflect a molecular basis of disease that may be detectable in biological specimens. Identifying these molecular changes and how they correlate with and predict disease progression may allow better estimation of future disease trajectory, which would inform therapy and facilitate development of patient-specific treatment regimens. Applicant has identified systemic changes reflected in the blood that culminate in measurable pulmonary decline as children enter adolescence.

Described herein are novel disease predicting biomarkers, novel modeling of FEV, using FD analysis, and the combination of both biomarkers in statistical models that improve on FD analysis predictions of lung function decline.

In one aspect, a method for detecting protein expression in an individual diagnosed with cystic fibrosis is disclosed. The method may comprise the steps of obtaining a sample from said individual; and detecting expression in said sample of each protein of a protein set, wherein said protein set comprises one or more proteins in Table 1.

TABLE 1

Protein Isoform Name and Gene Name (Abbreviation)

| Protein isoform name | Gene name |
| --- | --- |
| Immunoglobulin alpha-1 heavy chain constant region | IGHA1 |
| kappa 1 immunoglobulin constant | IGKC |
| Immunoglobulin kappa light chain VLJ region | IGK |
| immunoglobulin lambda | IGL |
| Immunoglobulin lambda constant 2 | IGLC2 |
| Immunoglobulin lambda constant 3 | IGLC3 |
| Tight junction protein 3 | TJP3 |
| Alpha-1-acid glycoprotein 2 precursor | ORM2 |
| Signal-induced proliferation-associated 1-like protein 3 | SIPA1L3 |
| Plakophilin 4 | PKP4 |
| Inter-alpha (globulin) inhibitor H2 | ITIH2 |
| Absent in melanoma 1 protein | AIM1 |
| Actin filament-associated protein 1 isoform X2 | AFAP1 |
| Serine/threonine-protein phosphatase PP1-beta catalytic subunit | PPP1CB |
| Retinol-binding protein 4 | RBP4 |
| Fermitin family homolog 1 | FERMT1 |
| Actin, cytoplasmic 2 | ACTG1 |
| Transthyretin | TTR |
| Melanoma inhibitory activity protein 3 isoform X2 | MIA3 |
| Pleckstrin homology domain-containing family G member 1 isoform X3 | PLEKHG1 |
| Pleckstrin homology domain-containing family A member 5 isoforms X1-X9 | PLEKHA5 |
| Pleckstrin | PLEK |
| Zinc finger protein 295 | Zbtb21 |
| Protocadherin Fat 2 | FAT2 |
| Cadherin-related family member 2 isoform X1 | CDHR2 |
| Voltage gated calcium channel alpha 1F subunit | CACNA1F |
| Actin filament associated protein | AFAP |
| Heat shock 70 kDa protein 1-like | HSPA1L |
| EF-hand calcium binding protein 2 | EFCBP2 |
| Polyamine modulated factor-1 (PMF1) protein | PMF1 |
| Keratin 16 | KRT16A |
| Keratin 18 | KRT18 |
| DNA replication ATP-dependent helicase/nuclease DNA2 isoform X4 | DNA2 |
| Non-lens beta gamma-crystallin like protein | CRYBG1 |
| Bromodomain and WD repeat-containing protein 1 isoform X1 | BRWD1 |
| Collagen type V alpha 3 chain | COL5A3 |
| Collagen type IV alpha | COL4A |
| Dynein heavy chain 12, axonemal isoform X5 | DNAH12 |
| Serine/arginine repetitive matrix protein 1 | SRRM1 |
| Ras-related protein Rap-1A | RAP1A |
| AT-hook-containing transcription factor isoform 1 | AKNA1 |
| Coiled-coil domain-containing protein 18 isoforms X1-X7 | CCDC18 |
| Coiled-coil domain-containing protein 180 | CCDC180 |
| Patatin-like phospholipase domain-containing protein 2 isoform X1 | PNPLA2 |

In one aspect, the method may comprise the step of determining an expression level of one or more, or two or more, or three or more, or four or more, or five or more, or six or more, or seven or more, or 8 or more, or 9 or more, or 10 or more, or 11 or more, or 12 or more, or 13 or more, or 14 or more, or 15 or more or 16 or more, or 17 or more, or 18 or more, or 19 or more, or 20 or more, or 21, or more, or 22 or more, or 23 or more, or 24 or more, or 25 or more, or 26 or more, or 27 or more, or 28 or more, or 29 or more, or 30 or more, or 31 or more, or 32 or more, or 33 or more, or 34 or more, or 35 or more, or 36 or more, or 37 or more, or 38 or more, or 39 or more, or 40 or more, or 41 or more, or 42 or more, or 43 or more, or each protein in the protein set, wherein said method is predictive of one or more clinical parameters in said individual.

In one aspect, the method may comprise the step of comparing said expression level to a control value to obtain a combined score and/or a risk probability score. A principle component or similar analysis that combines all the data from more than one or all of the markers may be used as well to generate a score. The combined score may be used to assess strength of association between the expression level of one or more of the aforementioned proteins, and the clinical parameter of interest. In one aspect, the clinical parameter may be lung function decline. The risk probability score may be used to predict the degree of risk that an individual will have or develop lung function changes or other clinical events that are of interest during the progression of cystic fibrosis.

In one aspect, the one or more clinical parameters may be selected from $FEV_1$, BMI, PE, number of hospitalizations, antibiotic status, infection status, and/or other clinical feature of the disease. These parameters may be selected using statistical methods described herein.

In one aspect, the clinical parameter is lung decline, wherein an individual classified as being high risk for rapid lung decline is treated via more aggressive anti-inflammatory therapy and increased monitoring. It is well known that increased disease monitoring is associated with improved pulmonary status. Thus, those identified to be at risk for rapid decline would warrant more frequent clinical encounters to ensure that stability is maintained. In addition, those at risk of decline may have become colonized with new pathogenic bacteria. Identification of subjects at risk of pulmonary decline would trigger aggressive testing for new pathogens and treatment to stem pulmonary decline, for example, by administration of anti-bacterial agents that address the specific pathogenic bacteria in an individual.

In one aspect, the sample may be blood, serum, urine, plasma, PBMCs, BALF, nasal and/or lower airway brushings, sputum, GI biopsies, lung explants, and combinations thereof. The sample may be obtained using routine methods known in the art. Multiple samples may be obtained over a period of time, for example, once every day, once every other day, once a week, once every two weeks, once every three weeks, once monthly, or once every two months, or once every three months, etc.

In one aspect, the detection step is carried out using mass spectrometry. For example, electrospray/matrix-assisted laser desorption ionization mass spectrometry may be used, as described herein.

In one aspect, the methods described herein may be carried out via the use of a computerized device. For example, one or more of the combined score or risk probability score may be calculated using a computer.

In one aspect, the combined score and risk probability score may be used to create a predictive model within a web browser, and wherein said computer comprises a graphical user interface (GUI) in which an end user can interactively explore said predictive model within said web browser. In one aspect, the end user may be, for example, a physician, patient, or patient guardian. The end user may use the interface to interactively explore the predictive model within a web browser. In an exemplary embodiment by Applicant, the GUI is called the Cystic Fibrosis Point of Personalized Detection (CFPOPD). Predictions may be generated on an individual basis, utilizing data from CF cohorts, such as the Cystic Fibrosis Foundation Patient Registry, and the user can select which patient for which the prediction model is graphically illustrated. Inputs include but are not limited to clinical and demographic characteristics, such as those from electronic health records, and large-scale data from proteomics.

Figure 13:
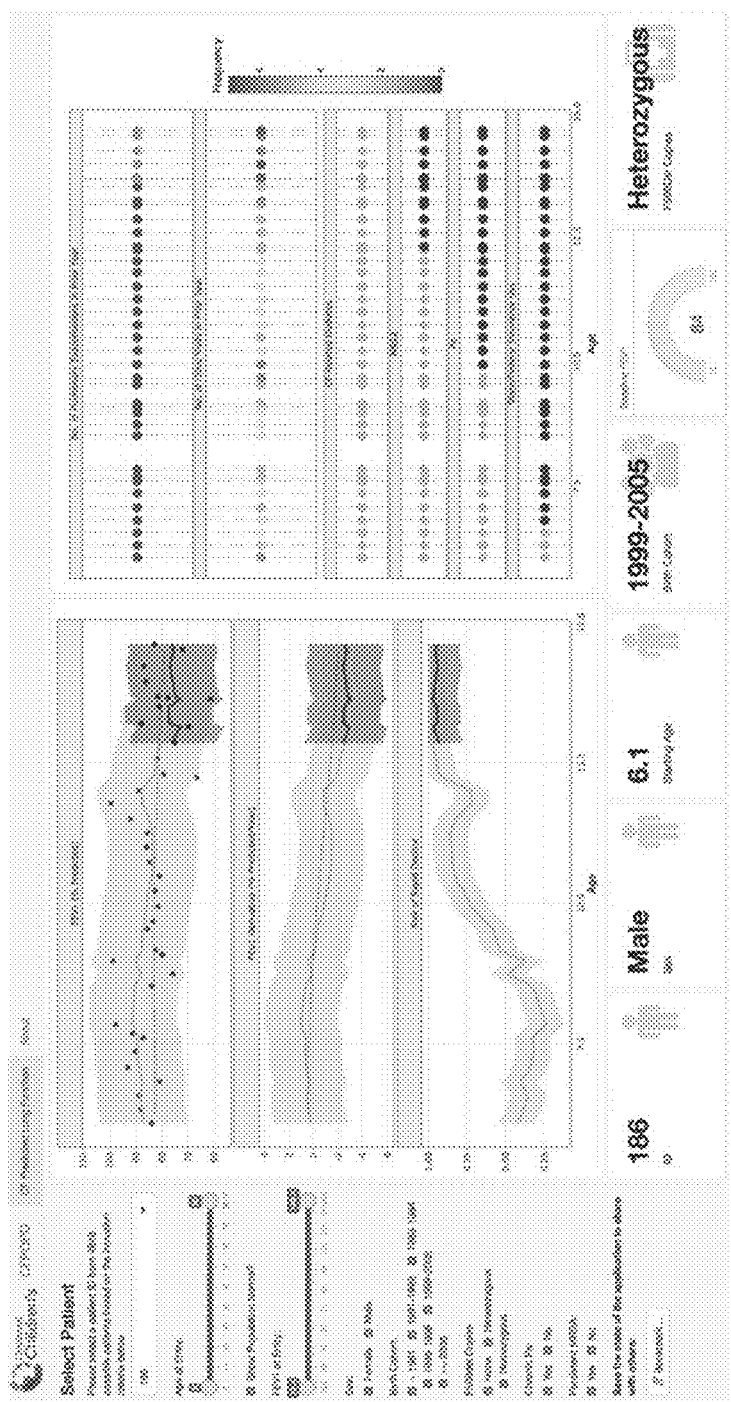
FIG. 13. GUI Prototype. The GUI was composed using the R statistical programming language, specifically using the flexdashboard, shiny, and plotly packages. See R Core Team (2017). R: A language and environment for statistical computing. R Foundation for Statistical Computing, Vienna, Austria. URL https://www.R-project.org; Barbara Borges and J J Allaire (2017). flexdashboard: R Markdown Format for Flexible Dashboards. R package version 0.5.1. https://CRAN.R-project.org/package=flexdashboard; Winston Chang, Joe Cheng, J J Allaire, Yihui Xie and Jonathan McPherson (2017). shiny: Web Application Framework for R. R package version 1.0.5. https://CRAN.R-project.org/package=shiny; Carson Sievert, Chris Parmer, Toby Hocking, Scott Chamberlain, Karthik Ram, Marianne Corvellec and Pedro Despouy (2017). plotly: Create Interactive Web Graphics via 'plotly.js'. R package version 4.7.1. https://CRAN.R-project.org/package=plotly

Measured and predicted lung function may be portrayed using three interactive graphs linked by a common timeline. FEV1, the FEV1 derivative, and the risk of rapid decline may all be displayed with corresponding shaded confidence bands. Additionally, the GUI may include patient-level and ecological descriptive variables as well as proteomic data that can be used to subset the pool of individual patients to select from, and the GUI may be expanded to include additional inputs. This facilitates, for example, the comparison of individually forecasted rapid lung function decline among individuals that are identical with respect to all model covariates expect for their sex. Both static and temporal covariates are displayed using graphical and text based panels. The GUI is currently available in prototype for public use at http://cfpopd.amazon-shiny.duckdns.org/ and a screenshot is contained in FIG. 13.

In certain aspects, the methods may be used in conjunction with evaluation of a drug or treatment for cystic fibrosis. For example, a potential treatment may be administered to an individual in need thereof, and the aforementioned methods may be carried out following administration of such drug or treatment.

In one aspect, a method for predicting evolution of a clinical parameter in an individual diagnosed with cystic fibrosis is disclosed. In this aspect, the method may comprise the steps of calculating a risk probability score from expression levels of a biomarker set comprising one or more biomarkers of Table 1; and classifying said individual into a high risk or low risk group based on the risk probability score; forecasting lung function trajectory based on said risk probability score. In certain aspects, the step may be performed on a computer. In one aspect, the clinical parameter may be lung function decline. In one aspect, the combined score may be based on at least two clinical measurements, or at least three clinical measurements, or at least four clinical measurements. The biomarker expression may be detected using methods known in the art, or using methods as set forth herein.

In one aspect, a method for segregating severe and disease in an individual diagnosed with cystic fibrosis is disclosed. The method may comprise the steps of detecting and quantifying a biomarker set comprising one or more proteins of Table 1, wherein said detecting step is carried out by assaying a biological sample from said individual and a clinical parameter obtained from said individual; and classifying the individual into a high or low risk group based on the combined score. The steps may be performed on a computer. In one aspect, the clinical parameter may be $FEV_1$ measurement force expiratory volume ($FEV_1$), and the method may be used to predict the risk of a rapid decline in $FEV_1$ in a said individual.

Calculation of Combined Score and Risk Probability Scores

A marginal score may be used to classify said individual as a high risk or low risk individual for rapid lung function decline and said combined score is used to perform feature selection wherein proteins are selected that correspond to said individual's risk of rapid lung function decline.

Marginal Score (Risk of Rapid Decline as High or Low).

In the first stage, $Y_{ij}$ may be a random variable representing lung function for patient i at time $t_{ij}$; i=1 . . . N; j=1 . . . $n_i$. For illustration, time refers to age (in years), but may be defined using other measures, including but not limited to: time since first pulmonary function measurement, in years; time since first serum collection, in years. In applying the calculation, it may be assumed $Y_{ij}$ is observed over one or more occasions, creating a random vector for each patient, represented as $Y_i$. In observation, these data may be sparsely or irregularly collected for various reasons, at the discretion of the user. Using Equation 1 (from Yao, Muller and Wang (2005)), the collection of lung function trajectories across patients observed at different time points can be expressed as follows. In one aspect, $X_i(T_{ij})$ may be the longitudinal process of $FEV_1$ for patient i at random time $T_{ij}$, which is measured with error $\varepsilon_{ij}$. This corresponds to the decomposition of longitudinal $FEV_1$ of Equation (1):

$$Y_{ij} = X_i(T_{ij}) + \epsilon_{ij} = \mu(T_{ij}) + \sum_{k=1}^{\infty} \xi_{ik} \phi_k(T_{ij}) + \epsilon_{ij}$$

where $\varepsilon_{ij}$ is residual error with mean zero and some variance $\sigma^2$; $X_i(\bullet)$, which is the function depicting the smooth, continuous longitudinal $FEV_1$ profile for patient i, can be characterized, for example, using a cubic b-spline basis with knot locations as described by Szczesniak and others (2013). Applying the PACE approach (principal components analysis through conditional expectation) as described by Yao, Muller and Wang (2005) to the longitudinal $FEV_1$ data outlined herein can be decomposed into functional principal component scores $\xi_{i1}, \ldots, \xi_{iK}$, where each score is a univariate quantity representing the $k^{th}$ harmonic depicting the $i^{th}$ patient's continuous longitudinal $FEV_1$ profile. These quantities correspond to said marginal scores and have been calculated previously for $FEV_1$ data from the Cystic Fibrosis Foundation Patient Registry, and the resulting scores can be used to classify said individual as high risk or low risk for rapid decline (Szczesniak et al.

2017). Techniques for choosing the number of harmonics, K, include, but are not limited to: cross validation.

Combined Score (Feature Selection According to Expression Level of Protein and Risk of Rapid Decline).

In one aspect, the $l^{th}$ protein of the $k^{th}$ patient may be represented as $P_{li}$, and $P_l$ may be the vector combining measurements of this protein across all patients. Similarly, the functional principal component scores (said marginal scores) for the $k^{th}$ component across all patients may be the vector $\xi_k \cdot \rho_{kl}$ may be the correlation coefficient representing the bivariate association between $\xi_k$ and $P_k$. Methods to estimate $\rho_{kl}$ include, but are not limited to, Spearman's rank correlation coefficient and Pearson's correlation coefficient, such application being readily understood by one of ordinary skill in the art. Said coefficient $\rho_{kl}$, with estimated value denoted as $\hat{\rho}_{kl}$, represents said combined score from this two-stage process for a given protein with the FEV$_1$ trajectory. Implementation of the approach can proceed using R (R Foundation for Statistical Computing, Vienna, Austria).

In one aspect, a risk probability score may be obtained using the following Equation (2):

$$Y_{ij} = X_i(T_{ij}, Z_{ij}) + \epsilon_{ij} = \mu(T_{ij}, Z_{ij}) + \sum_{k=1}^{\infty} \xi_{ik} \phi_k(T_{ij}, Z_{ij}) + \epsilon_{ij},$$

Obtaining said combined score may further include the step of inputting data for one or more clinical parameters of the individual. The marginal and combined scores, further including the step of inputting data on one or more clinical parameters, can be derived from a two-stage process. Stage I. Let variables be defined as in Stage 1. Additionally, let input data from one or more clinical parameters, such as observed body mass index percentile, be represented as Zij. The input will take the form of a vector if inputting data from one clinical parameter, and will take the form of a matrix with dimension N×C if there are c=1, . . . , C clinical parameters. One or more covariates may be time-varying. Using technique and assumptions for mean-adjusted functional principal components analysis described by Jang and Wang, Equation (1) is expanded as Equation (2) above, where estimation can proceed as they describe based on Equation (2) above with stated changes to covariance accommodating Zit. Let $\xi_{ikc}$ be the functional principal component scores, where c denotes that these scores are covariate adjusted. Stage II. As described in Stage II, $\rho$kcl is estimated for bivariate association of resulting covariate-adjusted functional principal component scores, in which bivariate association is estimated between vectors $\xi$kc and Pl. Resulting estimate $\hat{\rho}_{kcl}$ represents combined score for a given protein with the FEV$_1$ trajectory, which further includes inputting data on one or more clinical parameters.

Obtaining said risk probability score may further include the step of inputting data for one or more clinical parameters of an individual.

Modifying notation from Stage I, $Y_i$ may be realizations of a longitudinal patient-specific process other than FEV$_1$, such as body mass index percentile. By Equation (1) and aforementioned approaches, this substitution yields principal component scores $\xi_{i1o}, \ldots, \xi_{iKo}$, where o indicates the given outcome process being analyzed as $Y_i$. Stage II. Modifying notation from Stage II, $\rho_{klo}$ may be the correlation coefficient representing the bivariate association between $\xi_{ko}$ and $P_k$. Using the method described in Stage II, coefficient $\rho_{klo}$, with estimated value denoted as $\hat{\rho}_{klo}$, represents said combined score from this two-stage process for a given protein with the outcome process noted as o.

Additional Clinical Parameters as Inputs.

If using additional clinical inputs as described above (paragraph 0035) and letting $Y_i(t)$ be realizations of a longitudinal patient-specific process over time t other than FEV$_1$, such as body mass index percentile, yields covariate-adjusted combined scores for a different clinical endpoint. Resulting estimate $\hat{\rho}_{klco}$ represents combined score for a given protein with the outcome process noted as o, which further includes inputting data on one or more clinical parameters as covariates.

Derivation of Risk Probability Score.

Let $Y_{ij}$ represent FEV$_1$ for a given patient and time point. Assume that the longitudinal FEV$_1$ process follows the Gaussian linear mixed model with non-stationary covariance as defined by Diggle, Sousa and Asar (2015). The prediction algorithm to obtain said risk probability score can be defined through the following sequence of equations:

$$Y_{ij} = f_i(t_{ij}) + U_i + W_i(t_{ij}) + \epsilon_{ij} = g(t_{ij}) + P_{ij}^T \beta + U_i + W_i(t_{ij}) + \epsilon_{ij}, \quad \text{Equation (3):}$$

where $f_i(t_{ij})$ is the mean response function for the patient's longitudinal lung function process; $U_i$ is a patient-specific random intercept term, allowing patient profiles to deviate randomly from one another; $W_i(t_{ij})$ is a stochastic process characterizing the change in said individual's lung function process that cannot be explained by $f_i(t_{ij})$ alone; $\epsilon_{ij}$ is residual error from the model. In the second part of the equation, $g(t_{ij})$ is a nonparametric function representing a smooth, continuous-time process for lung function, which may be estimated using cubic b-splines; $P_{ij}$ is the covariate information on a single protein or set of proteins, corresponding to a vector or matrix, where T implies taking the transpose; $\beta$ is the vector of parameter coefficients corresponding to associations between lung function and protein expression level(s). Assuming $W_i(t_{ij})$ follows integrated Brownian motion, it follows that the derivative of this quantity in Equation (3) will yield Brownian motion, denoted $B_i(t_{ij})$ for the $i^{th}$ subject and $j^{th}$ time point. Then, the risk probability score is defined as $$P_r(B_i(t_{ij})) = P_r(B_i(t_{ij}) < \delta_i - f_i'(t) | \mathcal{H}_i(t)) \quad \text{Equation (4):}$$

where $\delta_i$ is certain threshold for the rate of decline, which may be patient specific (hence i subscript) or uniform for all patients; $f_i'(t)$ is the first derivative of the process from the model structure in Equation (3) and $H_i(t)$ is all protein expression covariate history before a given time on the $i^{th}$ patient. Protein expression levels may either be observed cross-sectionally or longitudinally.

Quantifying Uncertainty of Risk Probability Score.

Pointwise confidence intervals for the patient-specific risk probability score defined in Equation (5) can be derived as follows. Without loss of generality, assume this derivation is for a 95% pointwise confidence interval. Let $\mu_{B_{it}}$ and $\Sigma_{n_i}$ denote the mean and variance for $B_i(t_{ij})$ given $H_i(t)$. We assume the mean $\mu_{B_{it}}$ satisfies:

$$\sqrt{n_i}(\hat{\mu}_{B_i} - \mu_{B_i}) \xrightarrow{D} N_{n_i}(0, \Sigma_{n_i}) \quad \text{Equation (5):}$$

where $\mu_{B_i}$ denotes the vector $$\mu_{B_{i1}}, \ldots, \mu_{B_{in_i}}, \hat{\mu}_{B_i}$$

$\hat{\mu}_{B_i}$ is the estimate of $\mu_{B_i}$, and $n_i$ is the sample size for $i^{th}$ patient.

For each patient i, let $\hat{\Sigma}_{n_i}$ denote the estimation of $\Sigma_{n_i}$ from estimating parameters in the model from Equation (3) and taking derivatives of the relevant probability risk score quantities in Equation (4). The bootstrapping process to obtain a 95% confidence interval for risk probability is below.

(1) Sample B-independent samples, $Y_{n_i 1}, \ldots, Y_{n_i B}$ from $N_{n_i B}(0, \Sigma_{n_i})$, B=1, ... 100, and define parameter $\mu_{B_i}^* = \hat{\mu}_{B_i} + n^{-1/2} Y_{n_i b}$ (2) For each sample $Y_{n_i b}$, calculate $\Pr^*(B_i(t_{ij}))$ using $\mu_{B_i}^*$ by Step (1) above and calculate mean square error (MSE) for $\Pr^*(B_i(t_{ij}))$ as $\widehat{MSE}_{n_i}^* = B^{-1} \Sigma_{b=1}^{B}[\Pr^*(B_i(t_{ij})) - \Pr(\widehat{B_i(t_i)}))]^2$.

(3) Construct the 95% confidence interval for risk probability by $P_r(\widehat{B_i(t_i)})) \pm z_{0.975} \sqrt{\widehat{MSE}_{n_i}^*}$.

In one aspect, the risk probability score may be calculated using an algorithm which further includes the step of inputting data from one or more clinical parameters of said individual.

Derivation of Risk Probability Score.

Additionally define $Z_{it}$, wherein additional inputting data on clinical parameters, such as observed body mass index percentile, are represented as $Z_{ij}$. The input will take the form of a vector if inputting data from one clinical parameter, and will take the form of a matrix with dimension N×C if there are c=1, ..., C clinical parameters, and $Z_{ij}$ may include covariates that are time-varying. To accommodate the additional inputs, Equation (3) can be expanded as:

$$Y_{ij} = f_i(t_{ij}) + U_i + W_i(t_{ij}) + \epsilon_{ij} = g(t_{ij}) + P_{ij}^T \beta_P + Z_{ij}^T \beta_Z + U_i + W_i(t_{ij}) + \epsilon_{ij} \quad \text{Equation (6):}$$

where $\beta_Z$ is the parameter vector representing associations between each clinical input variable and the longitudinal lung function process.

It follows that the risk probability score can be modified to include covariate history by expanding Equation (4) as follows:

$$P_r(B_i(t_{ij})) = P_r(B_i(t_{ij}) < \delta_i - f_i'(t) \mathcal{H}_{iP}(t) \cdot \mathcal{H}_{iZ}(t)) \quad \text{Equation (7):}$$

wherein covariate history from the clinical, protein expression, and previous outcome inputs are represented as $H_{iP}(t)$ and $H_{iZ}(t)$, respectively. Although it is suppressed in Equation (7), the expression includes previous outcome history prior to the time point $t_{ij}$.

Quantifying Uncertainty of Risk Probability Score.

Boot-strapped estimates for covariate-adjusted risk probability scores can be computed as in Equation (5).

8. Risk Probability Score May be Performed for Another Clinical Outcome.

Modifying notation from above, let $Y_{ij}$ be realizations of a longitudinal patient-specific process other than $FEV_1$, such as body mass index percentile. By Equations (3) and (4) and approaches therein, the patient-specific risk probability score can be expressed as:

$$P_r(B_{io}(t_{ij})) = P_r(B_{io}(t_{ij}) < \delta_{io} - f_{io}'(t) \mathcal{H}_{io}(t)) \quad \text{Equation (8):}$$

where elements correspond to the terms defined in Equation (4) but for a different outcome o than $FEV_1$. Bootstrapped estimates for risk probability scores based on outcome o can be computed as in Equation (6).

Equation (8) and approaches herein can be adapted using the procedure set forth above to acquire covariate-adjusted estimates of risk probability for clinical outcome o.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Applicant analyzed serum samples from CF patients with severe (n=44) or mild (n=44) lung disease. Serum protein was purified via gel separation and liquid chromatography. Protein isoforms were identified using a cut off of at least 100 mass signatures per protein, coverage ranging from between about 15 and 100%. A combination of gel-based and MS-based label free quantitation was used to quantify the proteins. Pathways including the dataset members were analyzed.

In an exhaustive analysis of 61,942 serum protein isoforms, Applicant discovered a number of novel markers of CF lung disease severity and inflammation, and found that combining their measurement (either grouped or individually depending on the marker) with Functional Data (FD) Analysis of $FEV_1$ can predict lung function decline by 6-18 months in advance. Applicant hypothesized that characterization of blood protein expression and modification in longitudinal samples integrated with monitoring of $FEV_1$ changes over time and through FD analysis can provide a sensitive and specific algorithm that predicts risk of CF lung disease progression which can be used to inform therapeutic intervention. Applicant has developed a novel statistical model to predict $FEV_1$ decline that have now been modified to include the novel biomarkers, and which can be adapted to include use of other clinical parameters besides $FEV_1$ to predict disease progression.

In particular, Applicant has identified and validated serum proteome changes in banked samples collected from patients with stable and declining $FEV_1$, developed a dynamic prediction model by integrating analyses of validated proteomic data with Functional Data (FD) analysis of longitudinal $FEV_1$ data to produce a novel diagnostic algorithm that identifies individuals at risk of lung function decline, and has evaluated the capacity of dynamic prediction modeling to identify CF patients who develop rapid pulmonary decline during adolescence in banked patient samples, testing the performance of the markers in banked samples from the EPIC study. Applicant's studies have the potential to fundamentally shift the nature of CF care from an evidence-based model of care decisions to individual patient-based care decisions informed through a predictive molecular and lung function disease platform and/or other clinical parameters. The disclosed algorithms of predictive biomarkers may be used to inform therapy choices and significantly improve CF care.

Proteomic studies are conducted with LC MS/MS tandem mass spectrometric examination of patient serum. Each sample is split into 3 fractions which are analyzed by MS for 15 hours (including 3 technical replicates, 3 quality controls, and 2 wash runs preventing carry over). This allows deep screens to be conducted that capture information on approximately 7,000-10,000 protein isoforms and modification per sample with high confidence and accuracy, and allows capture of low-level proteins where differences are more often found when comparing disease severity cohorts. These analyses are far more rigorous than the usual "service center" analysis, generating approximately 7-10 times more data. This increased data collection also increases the time for analysis (~10 fold), but provides rigor for detection of useful biomarkers and decreases false discovery rates, markedly increasing chances of success. For Functional Data (FD) and Functional Principle Component (FPC) analyses of $FEV_1$, Applicant's preliminary analyses build upon FD analysis and longitudinal models that have been applied to the CF Foundation Patient Registry (CFF-PR). Further analyses of the available cohort data at hand, providing strong evidence of associations and feasibility. The modeling disclosed herein blends established biostatistical approaches with modern FD approaches to characterize the nonlinear $FEV_1$ trajectory of individual patients and predicts subsequent decline. The disclosed methods may be used for in-clinic applications for decision aids for pre-clinic planning and at the time of patient encounters. Marker data correlation with $FEV_1$ was measured in multiple simulations and by appropriate statistical tests as described.

CF is a recessive heritable disease that affects ~30,000 individuals in the United States. The primary defect results from mutations of the cystic fibrosis transmembrane conductance regulator gene, which codes for the CFTR chloride channel. The protein is expressed predominantly on the apical surface of epithelial cells throughout the body (although low level expression has been detected in other tissues). Over 2,000 disease causing mutations have been identified in the CFTR gene, with the majority of patients (~90%) exhibiting at least one allele with the F508del mutation (1). Disease causing mutations fall into 5 classifications that result in abnormal CFTR protein that is either truncated, misprocessed/mislocalized, defects in channel gating or conductance, or improper gene splicing. CF is diagnosed at birth via newborn screening. While the determinants of disease are well characterized, forecasting disease progression has to date been unsuccessful (2; 3).

Three important measures are used in monitoring CF disease progression and response to therapy; $FEV_1$, PE frequency, and BMI. Although these measures (particularly) lung function ($FEV_1$), have demonstrated steady improvement over the past two decades, a rapid deterioration of lung function persists, especially during adolescence (FIG. 2). While there are several potential interpretations for this observation, without intending to be limited by theory, it is believed that systemic changes reflected in the blood culminate in measurable pulmonary decline during this period (10-19 years of age).

Figure 3:
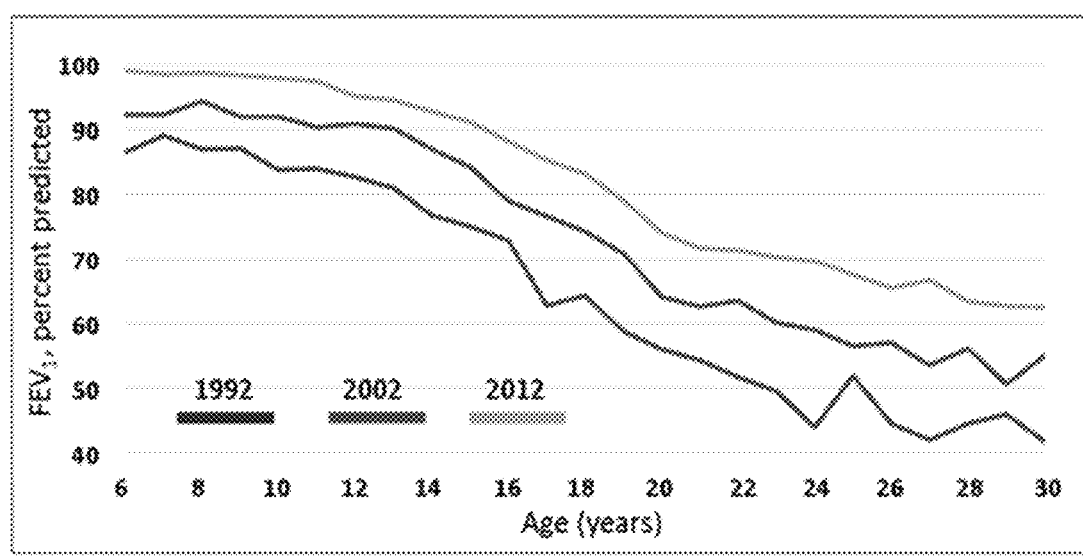
FIG. 3. Lung function decline with age. Comparison from data compiled in 1992, 2002, and 2012. Despite improvement in lunch function at early age, the rate of decline is unaffected by modern therapies. Source: CF Foundation Patient Registry data.
Figure 4:
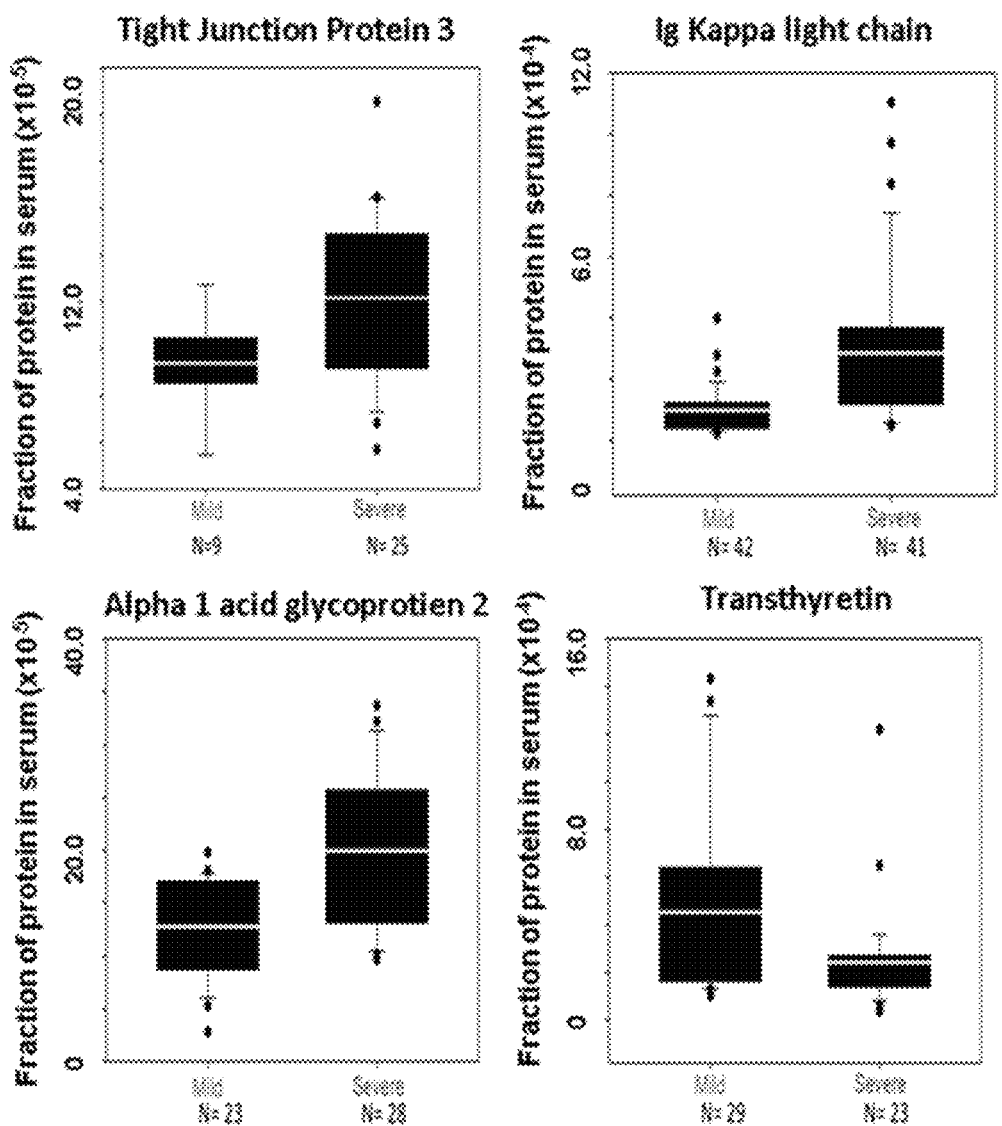
FIG. 4. Box plots of CF disease severity serum biomarkers. Example of differential expression identified serum biomarkers of lung disease severity. Forty-four candidates whose quantities differ by 0.35-5.4-fold between mild and severe disease have been identified.

Care for CF patients has advanced rapidly over the past two decades, with an unprecedented increase in patient longevity and quality of life. The reasons for these improvements include: a robust CFF-PR that collects data from nearly all CF patients in the US, allowing assessment of outcomes and treatment responses; standardization of care & therapies; and dramatic advances in new CF therapeutics, especially genotype-specific CFTR modulators such as KALYDECO® (4) and, to a lesser extent, ORKAMBI® (5). These advancements have increased the median survival of CF patients to 41 years (CFF-PR—2014), and >50% of CF patients alive today are adults. In many respects, research and care to improve CF patient outcomes has become the model for other rare diseases. Accompanying the improvements in CF outcomes are a number of challenges that urgently require attention. There have been dramatic global improvements in the CF disease trajectory (FIG. 3), but many patients have not fully benefited. Indeed, the average age of death of CF patients in a given year has remained remarkably static, with most patients dying of CF lung disease during their third decade of life (CFF-PR 2014 statistics).

The burden of care also remains a significant challenge, as most adolescents and young adults need to spend approximately two hours daily dedicated to therapies that maintain health. Adherence to complex care regimens is often untenable, and this has led to the need to 'personalize' care such that patients commit to daily therapies that are most likely to benefit them individually. These commitments increase during periods of instability, and treatment of PE remains highly interruptive to daily care and negatively impacts quality of life. They also are sentinel markers of disease progression, as 25% of CF patients fail to recover lung functions following PEs (6). The benefits of care improvements have also challenged the capacity to monitor CF lung disease and CF manifestations in other organs. Assessing the relative benefit of new therapies in the context of relatively normal lung function (as measured by routine spirometry) is particularly challenging for CF providers. This requires the development of more sensitive tools to identify subjects most likely to benefit from various interventions and to monitor the impact of new therapies selected for care plans. Finally, the conduct of clinical trials to advance CF outcomes and interventions can no longer rely on standard outcome measures such as $FEV_1$, as excessively large and/or long clinical trials are needed to demonstrate improvements. Thus, the CF field stands at a crossroads, where the benefits of the past limit the capacity to advance therapies and personalize care when relying upon standard measures of disease status. The disclosed methods address these gaps, seeking to produce vertical advancement in disease monitoring and prediction through the use of advanced biostatistical modeling of lung function coupled with novel molecular biomarkers. The disclosed methods may be used to identify those patients most likely to benefit from various interventions, and allow clinicians to monitor responses to precise and personal interventions.

Applicant modified proteomic approaches (7-17) to examine serum from CF patients with mild or severe lung disease (13). Based on the experience of others in the cancer and cardiovascular fields, where conventional "shotgun" proteomics (identifies 500-1000 proteins per sample) failed to distinguish disease severity in cohorts exhibiting the same disease, Applicant hypothesized that deeper screens would be necessary for CF studies. A proteomic analysis protocol was developed, involving multidimensional separation of proteins by abundant protein-adsorption columns and gel and column chromatography. This approach generated multiple fractions from each sample that were subjected to 15 hours of mass spectrometric analysis.

The following is a description of an exemplary proteomic analysis of CF patient serum. The approach may be applied to the analysis of any biological sample, for example, plasma, urine, cells, and other tissues. The methodology involves novel modifications of previously described approaches (Ziady A G, Sokolow A, Shank S, Corey D, Myers R, Plafker S, Kelley T J. Interaction with CREB binding protein modulates the activities of Nrf2 and NF-kappaB in cystic fibrosis airway epithelial cells. Am. J. Physiol Lung Cell Mol. Physiol 2012 Jun. 1; 302(11): L1221-L1231. PMCID:PMC3379036; Chen J, Kinter M, Shank S, Cotton C, Kelley T J, Ziady A G. Dysfunction of Nrf-2 in CF epithelia leads to excess intracellular $H_2O_2$ and inflammatory cytokine production. PLoS. One. 2008; 3(10): e3367; Ziady A G, Kinter M. Protein sequencing with tandem mass spectrometry. Methods Mol. Biol. 2009; 544:

325-41). Biological fluid or tissue lysate can be adsorbed for albumin or other highly expressed proteins using absorption columns. Protein may be precipitated from eluate or lysate with acetone (equilibrated to 90% acetone), dried, and rehydrated at a concentration of 5 mg/ml in 8 M urea, 2% CHAPS, 50 mM DTT in water. Greater than 45 ug of protein for a sample is generally subjected to SDS-PAGE, excised gel fragments containing all the protein from the sample are reduced and alkylated (to achieve more fractionation more gel fragments are cut), and subjected to in-gel tryptic digestion (20 ug/ml), and protein peptides are extracted for LC MS-MS. Extracts were acidified by equilibration in 0.1%-1% acid (e.g. acetic or formic acids), loaded onto a fractionation column (e.g. Thermo Fisher Scientific Acclaim PepMap $C_{18}$ column) at a flowrate of 0.15-0.5 ul/min, and subjected to nanospray tandem mass spectrometry with a mass spectrometer (e.g. Thermo Fisher Scientific LTQ Velos Pro spectrometer). Analysis in conducted in data-dependent mode capturing the 3-12 most abundant parent ions from full MS scans for fragmentation by collision induced dissociation (CID). Each gel fragment is run 3-9 times, and the data files from all runs are pooled for database analyses. In addition to multiple fractionation steps we use mass tolerance of 0.1-2.0 Da for parent ions and 0.01-0.7 Da for fragment ions to enhance the ability to quantitate low level proteins. Identified protein isoforms using 2-100% coverage cut off with >2 mass signatures per protein.

The EPIC Observational study includes >1,000 patients with annual blood samples for >10 years linked to the CFF-PR. 44 mild ($FEV_1$>85th percentile among CF patients) and 44 severe (<45th percentile) patient cohorts were matched based on age, gender, genotype, and *P. aeruginosa* infection status, then randomized and blinded before proteomic analysis. Applicant identified a total of 61,942 protein isoforms expressed across both cohorts, with 4751 proteins identified in at least half the subjects of each cohort. Data were normalized to a relative abundance (RA) measure (0 to 1) for each sample. For each isoform, RA was summarized (mean RA, number with RA>0, ratio of RA mild/severe) and, to reduce the data, a battery of paired statistical tests was performed on the matched samples: McNemar's, Wilcoxon Signed-Rank, paired Student's t test, and permutation of the difference.

Figure 5:
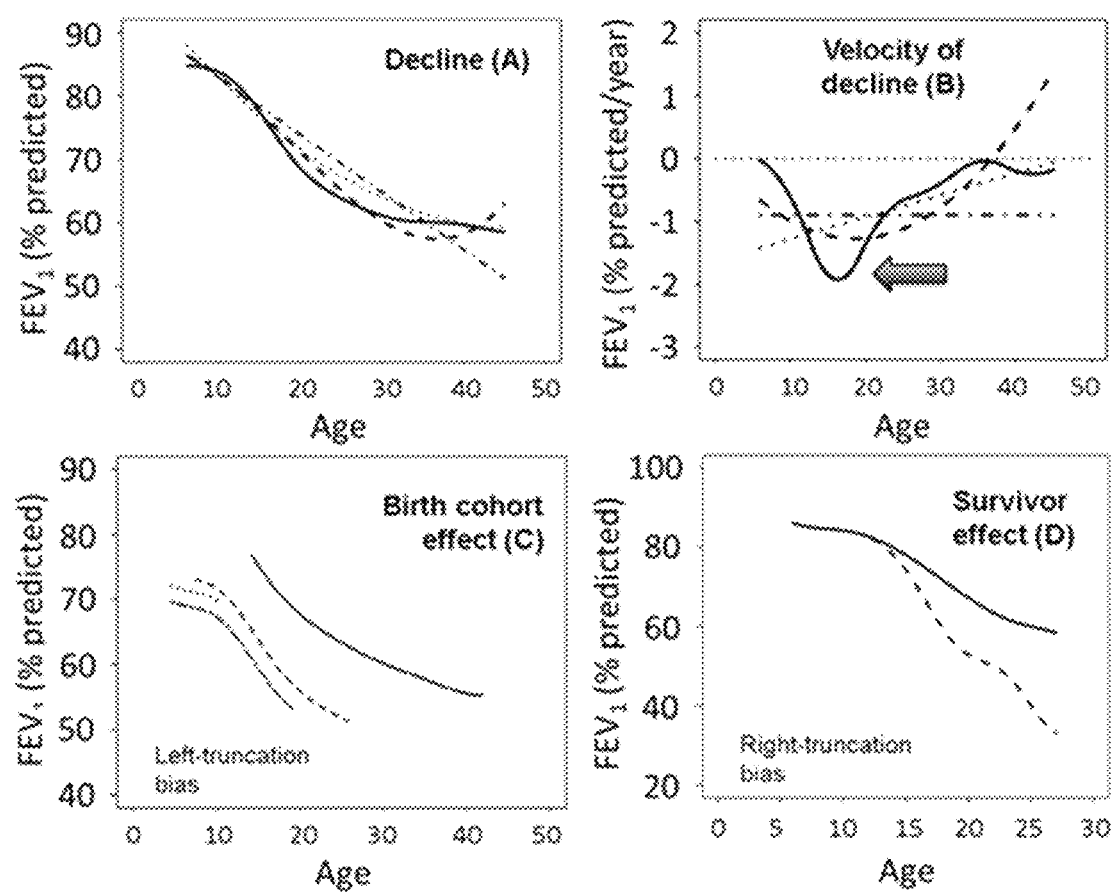
FIG. 5. FD analysis model is superior to presently available models of lung function decline. CFFPR analyses with point estimates from FD analysis (solid line), cubic (dashed line), quadratic (dotted line) and conventional linear (dot-dash line) mixed models of decline (A) and rate of decline (B); stratified by birth cohorts born before 1981 (solid line), 1981-1988 (dashed line), 1989-1994 (dot-dash line), and after 1994 (dotted line) (C); stratified by survival (solid line) and death (dashed line) for patients less than 19 years of age (D). The FD model in (A) reflected the dynamic status of lung function during young adolescence/early adulthood; traditional models found no changes and even indicated gains in lung function (e.g. cubic). The arrow at the "dip" in (B) shows 1) Patients attained most rapid decline at median age (IQR) 16.3 (13.5, 21.0) years; 2) Degree of maximal $FEV_1\%$ loss was variable (mean: 1.98% pred/yr, 95% CI: 1.86, 2.10). Longitudinal $FEV_1\%$ measures shared correlation for up to 9 years, highlighting the potential of short-term clinical interventions to impact long-term lung function. Further subgroup analysis revealed that $FEV_1\%$ curves vary according to survivorship and birth cohort (C-D), highlighting left- and right-truncation biases, respectively.

In addition, a two-fold approach was used to identify protein isoforms as candidates for improved prediction of FEV1. Functional principal components (FPC) scores were correlated with each protein expression level as described in [0049], measured using correlation coefficient $\hat{\rho}_{kcl}$. In addition, these isoforms were included as covariates in one-at-a-time modeling of Equation (3) described in [0049]. These analyses generated the newly discovered 44 isoforms above which are the first serum biomarkers of CF disease severity identified by nonbiased analysis, and are the basis for developing a lung function decline prediction model. Furthermore, the protein isoforms identified are baseline biomarkers of disease that segregate with disease severity when patient are stable. This is far more advantageous than presently available biomarkers such as C-reactive protein, which are only useful during acute exacerbation (20-24). The initial twenty biomarkers identified exhibited areas under the curve (AUC) of 0.69 or higher. These AUC values indicate that the biomarkers are superior to presently available markers of disease (21-24). Many of the biomarkers have either physiological or biological connections to CF (FIG. 5). For example, tight junction protein (TJP) 3 contains a PDZ motif and is a member of a family of proteins that interact with CFTR (25). Increases in serum IgG Kappa light chain levels are associated with chronic inflammation (26). Alpha-1-acid glycoprotein 2 is one of 4 biomarkers used to predict inflammation and mortality beyond CF (27), and transthyretin has been shown to be significantly decreased in CF patients compared to non-CF (28). Excessive inflammatory signaling in CF and an increase in patients with severe disease would be expected and is suggested by our nonbiased biomarker identification.

CF lung disease demonstrates a steady decline that typically manifests during adolescence and young adulthood (29); however, rapid decline, characterized by accelerated loss of lung function relative to center-specific and/or population norms, is a ubiquitous event in the lives of patients (FIG. 1). Identifying when patients are at highest risk for rapid lung function decline is a significant gap in CF research, and offers the opportunity to intervene prior to irreversible lung damage. A key contributor to this gap has been the paucity of individualized predictive data on the specific timing and severity of lung function decline, and this is sustained by continued reliance on linear statistical approaches to fit nonlinear lung function decline (30). Moreover, phenotypes of patients at risk for rapid decline have not been well defined due to the analytically complex progression of CF (31).

In contrast to historical approaches, Applicant's biostatistical research on CF lung disease progression has been based on nonlinear longitudinal data analysis methodology and implementation in CF clinical/translational research. Applicant's approach fuses longitudinal data analysis together with FD analysis (32), a branch of statistics that offers tools to characterize nonlinear phenomena. FD analysis sheds light on complex pathophysiological relationships in different disease states, such as sleep disorders (33) and Alzheimer's disease (34).

Applicant has used the CFF-PR to demonstrate that FD analysis predicts CF lung-function decline with improved accuracy compared to traditional linear approaches (35) and can be used to identify phenotypes of rapid decline. Historically, CF registries (such as the CFF-PR) have carefully maintained lung function data to track disease, but have not utilized data for prognostic care (36). The disclosed dynamic prediction models using FD analysis have leveraged this rich longitudinal data to develop more accurate tools that predict disease course and in turn help prioritize interventions for the individual patient (FIG. 5). The disclosed methods meaningfully contribute to CF precision medicine, an area that has been noticeably understudied (37).

Major advancements in personalized medicine in CF may change the clinical course of the disease (38). Applicant has successfully used FD analysis to characterize nonlinear population-level lung function decline of cystic fibrosis patients in the US. Applicant's CFF-PR study of over 30,000 patients and 500,000 $FEV_1$% measurements utilized longitudinal FD methods to address nonlinearity and serial correlation (35). Applicant estimated degree (velocity) and timing of rapid decline by taking derivatives in Applicant's model and traditional models. The covariance structure included exponential decay and random intercepts. The FD model was superior, compared to traditional models, in terms of estimating the onset and severity of rapid FEV1% decline and model validity (FIG. 5). Applicant's results indicate that nonlinear, heterogeneous lung disease progression prevails, and the ability of FD models to establish CF phenotypes predictive of rapid decline.

Applicant has further identified $FEV_1$ phenotypes corresponding to early, middle and late rapid decline in patients 6-21 years of age. Using the CFF-PR data, modes of variation in FEV$_1$ progression are characterized as functional principal components (39). The majority of variation (first functional principal component: 94%) among patient profiles are characterized by differences in mean longitudinal FEV$_1$ trajectories. Average degree of rapid decline was similar among phenotypes (roughly −3% predicted/year); however, average timing differed, with early, middle and late phenotypes experiencing rapid decline at 12.9, 16.3 and 18.5 years of age, respectively. Individuals with the late phenotype had the highest initial FEV$_1$ but experienced the greatest loss of lung function.

FEV$_1$ variation coupled with nonlinear progression over age produces an uneven, "saw-tooth" shape for each individual's trajectory (see FIG. 1), making it difficult to model the time-course of a patient's underlying lung function and utilize it for earlier detection and intervention. To further improve the predictive accuracy of rapid decline, Applicant utilized FD analysis to develop a dynamic prediction model of CF progression that accounts for the variation in FEV1. To leverage existing data for individual patient prediction, a dynamic prediction model recently proposed by Diggle et al (40) was expanded to accommodate the jagged, nonlinear shape of FEV$_1$ trajectories using CFF-PR data on 27,296 patients >6 years who each had 1 to 89 FEV$_1$ measurements. Covariates in the model were birth cohort, copies of delF508, baseline FEV$_1$, and male gender. Time-varying covariates included infections with Pa, MRSA, CF-related diabetes and use of state insurance as a marker of socioeconomic status. Interactions between each of these covariates with time were examined. To account for irregular follow up and occurrence of PEs, we included rolling, time-varying covariates for the numbers of follow up visits and PEs within the last year. Although these covariates are not commonly used in the literature, their inclusion improved predictive performance of the model based on residual analyses. All covariates were statistically significant (P<0.05) with the exception of state insurance (P=0.07).

Applicant evaluated predictive ability of the proposed stochastic model using a preliminary sample size of 36 subjects with available data on proteomic markers. These subjects contributed a total of 1975 FEV$_1$ longitudinal observations. The subjects were randomly split, with 80% contributing measurements to the training dataset for model building, and 20% providing data for the validation step. Using the training dataset, a model that included terms to model nonlinear progression of FEV$_1$ over age (cubic b-splines), a severity indicator established by the EPIC study (binary variable) was used; also included were terms for the markers and their interaction with age. Severe classification met statistical significance (P<0.05).

Predictive accuracy, measured using Akaike information criterion (AIC), was superior in this model compared to a model that excluded the proteomic marker terms. Validation metrics that were assessed in the test cohort included mean absolute deviation (MAD), root mean-square error (RMSE), mean absolute percentage error (MAPE) and correlation between predicted values and observed values. Based on the FEV$_1$ scale, validation metrics showed relatively small prediction error. MAPE, which measures forecast accuracy as percent difference between actual FEV$_1$ and predicted FEV$_1$, shows that there is relatively small error between projected and actual FEV$_1$ values. Correlation between observed and predicted values is excellent (above 0.80) and is significantly higher than presently available measures (range from 0.54-0.71).

Applicant also assessed the predictive value of our proteomic markers using FD and dynamic prediction as described above. A number of the biomarkers were included as covariates and their interaction with age in the Reduced Model. Other covariates included in the model were age-specific components to fit the FEV$_1$ trajectory, as shown in the FD analysis in previous studies, and the Mild/Severe designation from Applicant's original study. The model showed that proteomic markers were significantly associated with mean FEV$_1$ (coefficient: −8.03, SE: 4.07, z=−2.0, P=0.04) and approached significance in their association with FEV1 decline (coefficient for interaction: 1.03, SE: 0.79, z=1.3, P=0.19).

Figure 6:
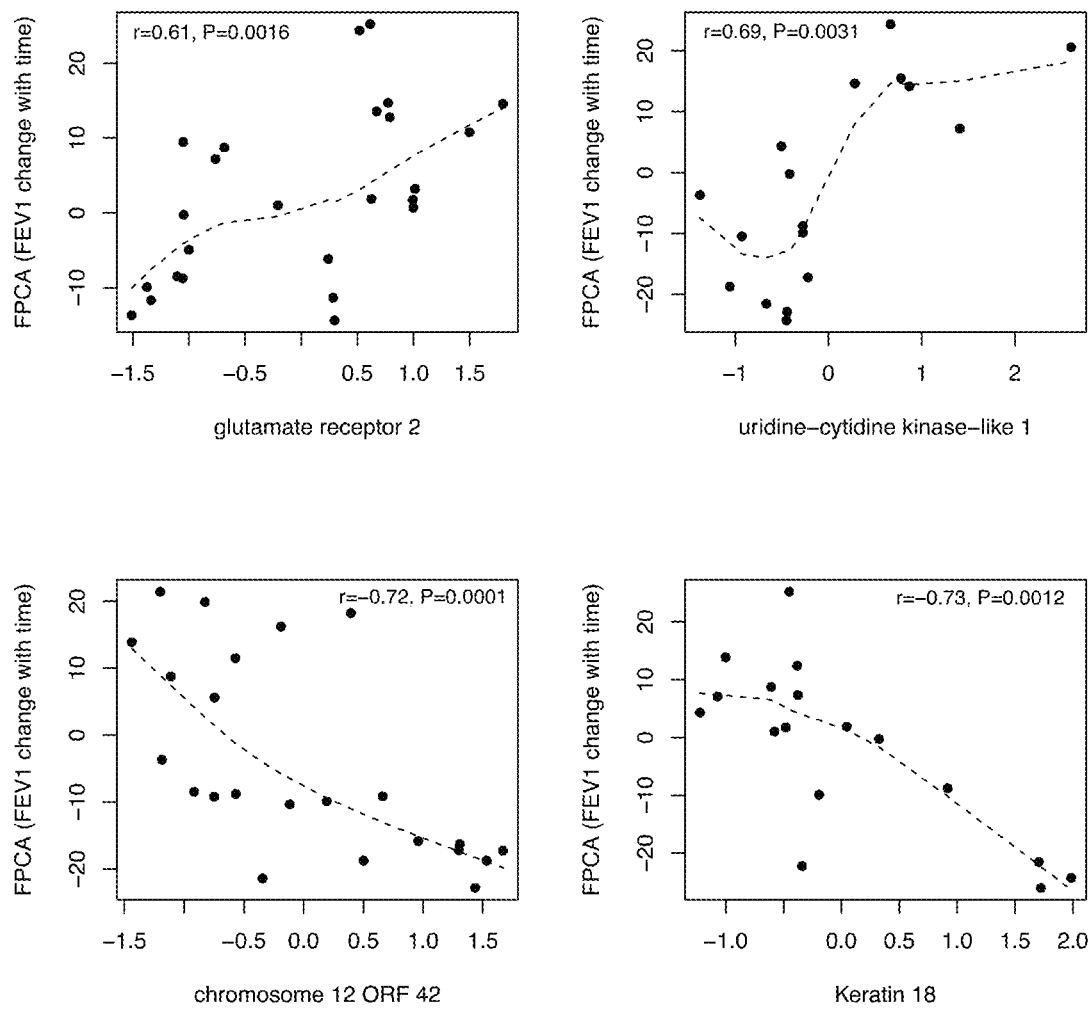
FIG. 6. Biomarker correlation with functional principle component (FPCA) analysis of lung function. Examples shown for 4 of 18 biomarkers discovered in preliminary cross-sectional proteomic analyses that significantly correlate with FPCA analysis of $FEV_1$. The first principle component score (FPC1, y-axis); the thick dashed black line is the fit to the data using a scatterplot smoother; positive association (r) indicates that higher values of these markers may lead to worsening $FEV_1$ trajectory, while negative associates (−4) indicates that higher values of these markers correspond to improvements in the $FEV_1$ trajectory. Although these studies were conducted in discovery mode to capture the maximal number of biomarkers, data on individual markers will only improve under targeted MS and ELISA analyses.

Serum proteome changes in banked samples collected from patients with stable and declining FEV$_1$ can be validated as follows. Preliminary studies generated serum biomarkers that segregate CF disease severity during periods of disease stability. Conduct of longitudinal analyses to validate the predictive power of our biomarkers in samples from the EPIC CF cohort may provide the confidence for future modeling. Proteomic discovery studies in 88 cross sectional samples identified 20 biomarker changes that segregated CF patient lung disease severity in adolescence. Data collected from proteomic screens can benefit statistical models of lung function decline. To determine the utility of the molecular markers, top 20 molecular biomarkers were examined for their ability to enhance lung function decline modeling. Initial studies are cross sectional and conducted in discovery mode. Multiple (>10) simulations of FPCA analyses of FEV$_1$ including data for each of the top 20 markers showed significant correlations between the behavior of our novel markers and FEV$_1$ decline (FIG. 6).

The discovery cross sectional data was collected by high throughput discovery mode MS analysis. Data from both targeted MS and ELISA may be integrated with FD analysis, either in combination or separately. Biomarkers discovered in preliminary cross-sectional studies for prediction of future FEV$_1$ decline, may be validated using targeted proteomics and ELISA analyses of banked serum samples from the EPIC Observational study.

Samples. Analysis of samples from EPIC can be used to evaluate the predictive capacity of the biomarkers 1-5 years in advance of cohort segregation by FEV$_1$. These can be compared with additional candidate biomarkers, and secondary analyses can be used to examine relationships to established predictors of disease severity, including PEs, BMI, and microbiology. The choice of the EPIC samples may be based on the availability of longitudinal samples for patients that cover the age range where significant lung-function decline is observed (e.g., early teen years). The longitudinal proteomic profiles can be categorized for subjects already profiled at 'baseline' or time zero. This will determine if the baseline protein markers are able to predict subsequent disease progression. Preliminary data using FEV$_1$ alone shows a fairly even distribution of different phenotypes to examine: stable high (n=16) and stable low (n=13) (total stable, n=29) and rapid lung-function decline among 'mild' lung disease subjects at baseline (n=10) and in those with more severe disease at baseline (n=12) (total 'decliners', n=22). The remaining patients (29 of the original 88) may be used to supplement the 'extreme phenotype' data and provide information on proteomic profiles across the continuum of clinical presentation.

Mass spectrometry. Proteomic analysis will follow the well-established flow of previous studies. Applicant has developed useful mass spectrometry-based approaches for the identification/quantitation of thousands of proteins in serum samples. Protein is prepared from serum using albumin adsorption columns and gel and column chromatography, followed by tryptic digestion. Following preparation of whole-serum protein, serum-protein peptides are extracted and subjected to data-dependent sequencing and mass spectrometry analysis, as previously described (7-9; 11; 13-17; 42). Briefly, the samples are loaded in a HPLC system autosampler and eluted by reverse-phase chromatography into a mass spectrometer fitted with a nanospray ion source for analysis. The mass analyzer is set up for a data-dependent mode using dynamic exclusion settings: repeat count=1; repeat duration=0.5 minutes; exclusion list size=50; exclusion duration=1.5 minutes; exclusion mass width=1.5 amu. Collision-induced dissociation (CID) is used to fragment peptides, and CID spectra are searched against a human fasta database using Proteome Discoverer™ software. A decoy database is used to control for false discovery. A threshold filter of >2.0 for peptide XCorr score is used for sequence identification. For our preliminary studies, this produced a range of coverage for identified proteins of 5.15%-79.91% and an average of 10.03% for all proteins identified. This high stringency filter of our data provides more reliable quantitation, and aids the reduction of our data in follow-up statistical analyses.

Given the emphasis on early detection of rapid disease progression from the CF community, the availability of extensive demographic, clinical, molecular and environmental measurements from the EPIC data augmenting the CFF-PR, and the emergence of promising methodologic approaches for analysis, the disclosed methods allow for improved dynamic prediction models of rapid decline through integration of validated proteomic markers. Rosenfeld and colleagues (47) have utilized part of the EPIC cohort (n=946 patients who were Pa-negative at enrollment) to study associations between data collected in the year after the first pulmonary function test (PFT) and subsequent rate of $FEV_1$ decline (mean±SD follow up: 6.2±1.3 years). Through multivariable linear modeling of age-related $FEV_1$ progression with generalized estimating equations, they confirmed established risk factors for decline (e.g., female gender) and identified a new risk factor (*S. maltophilia*). Although this was a relatively young cohort (mean±SD age at entry: 7.9±2.0 years) with mild CF disease, they observed a similar "ceiling" effect to what was originally described by Konstan and colleagues and we previously found from our study.

Figure 7:
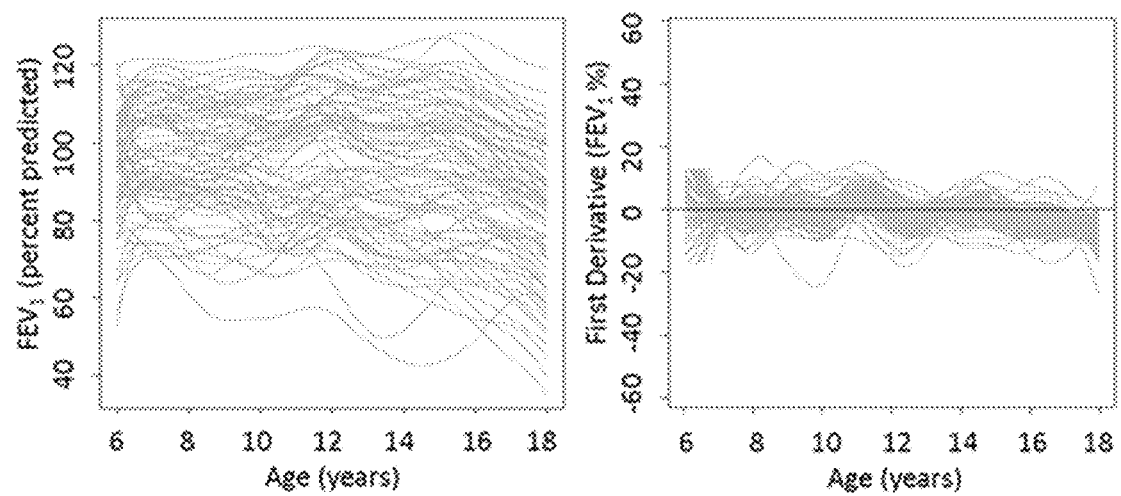
FIG. 7. On the left, smoothed $FEV_1$ observed over age (in years) for the EPIC cohort. On the right, the corresponding rate of change in $FEV_1$ (expressed as % predicted/year) over age.

Modes of variation in $FEV_1$ decline for the 88 EPIC subjects (44 Mild, 44 Severe, described above) with longitudinal PFT and cross-sectional proteomic data were examined using functional principal components, the FD analysis technique to the CFF-PR, in order to characterize rapid decline during adolescence and adulthood. Median (IQR) age at entry was 12.5 (9.8-15.3) years; follow-up ranged from 20 to 216 PFTs per patient. Individual smooth curves from the FD analysis had substantial variation between patients and within an individual patient over time (FIG. 7). The first functional principal component explained 85.3% of the variation in $FEV_1$, suggesting that the individual trajectories were similar to the overall mean curve but shifted according to initial $FEV_1$. The four subsequently ordered functional principal components, which reflect higher-order modes of oscillatory variation, explained 8.1%, 3.7%, 1.8% and 1.0%, respectively.

Rapid decline was observed in different periods of age for the majority of individuals in the cohort. Most rapid decline during the observation period occurred, on average, at 15.5±2.3 years of age, with decline of 3.9+4.2% predicted/ year. To understand how rapid decline in this cohort is related to proteomic markers, the association between each FD parameter and marker of interest was estimated using Spearman's r. To adjust for multiplicity in this preliminary analysis, associations with P<0.01 were considered statistically significant. Several associations were found between proteomic markers and the first functional principal component for $FEV_1$ (lower values of this component correspond to milder disease); several markers including glutamate receptor 2 isoform 4, alpha-1-acid glycoprotein 2 precursor, immunoglobulin alpha-1 heavy chain constant region, anti-*Entamoeba histolytica* immunoglobulin kappa light chain, anti-HBsAg immunoglobulin Fab kappa chain, AT-rich interactive domain-containing protein 4A isoform I, and uridine-cytidine kinase-like 1 isoform 2 were positively associated (range of r: 0.37 to 0.69); additional markers including unconventional myosin-XVIIIa isoform X1, chromosome 12 OPR 42, isoform CRA c, and Keratin 18 were negatively associated (range of r: −0.73 to −0.54). Degree of rapid decline was negatively associated with markers A-kinase anchor protein 3 and Keratin 18 (r: −0.76 and −0.72, respectively). Patients who experienced rapid decline at a younger age tended to have elevated levels of markers alpha-1-acid glycoprotein 2 precursor, anti-*Entamoeba histolytica* immunoglobulin kappa light chain, and anti-HBsAg immunoglobulin Fab kappa chain, corresponding to negative associations (range of r: −0.55 to −0.43), and lower levels of chromosome 12 open reading frame 42, isoform CRA c (r: 0.55) (see FIG. 6).

The disclosed dynamic prediction model uses patient-specific information from the EPIC cohort while incorporating parameter estimates from Applicant's recent large-scale CFF-PR study to predict the onset of rapid decline. The model takes into account observed lung function for the patient at each time point, the mean $FEV_1$ evolution for each patient, and encompasses covariates with corresponding association parameters. Normal distribution of the data provides patient-specific heterogeneity between $FEV_1$ trajectories. Furthermore, a stochastic process is used to reflect the "saw tooth" variation over time for individual patients (see FIG. 1); integrated Brownian motion is used to depict this process. Normally distributed measurement error from the PFT is accounted for. Finally, data for the level of markers is added to the model. The covariance functions and estimation algorithm have been described previously (40). The model for the CFF-PR is implemented using the lmenssp package (48) in R (R Foundation for Statistical Computing, Vienna, Austria). The covariates that considered from the CFF-PR may be expanded to include additional factors available from the EPIC study. Candidate molecular markers can be directly added as covariates, and the association parameters can be denoted to fit the model on smaller data. If marker data were available from all CFF-PR subjects, this new model could be called the "Full Model". A so-called "Reduced Model" can be fit using detailed data from the EPIC cohort.

Figure 8:
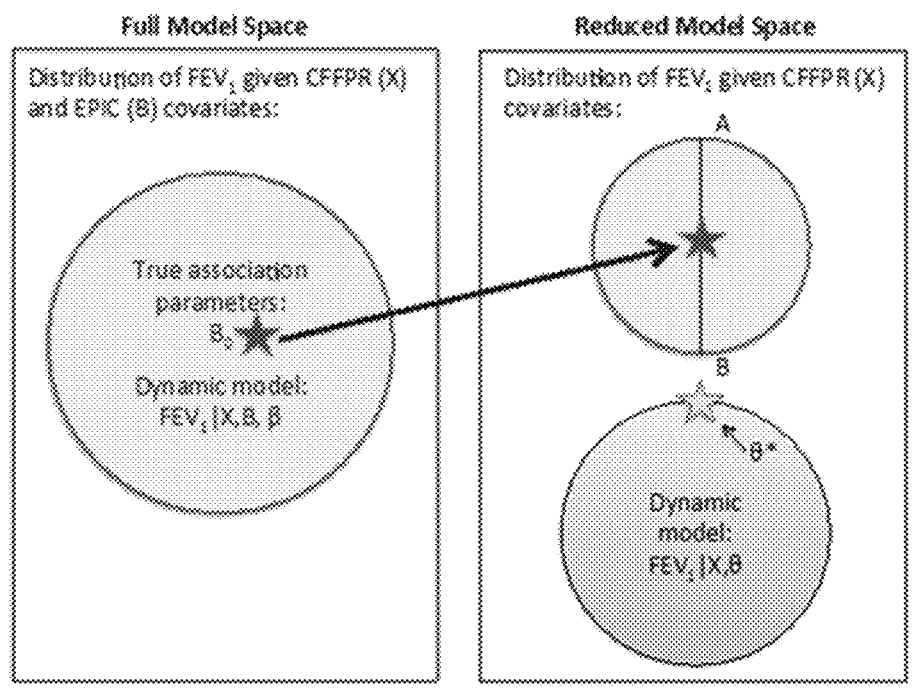
FIG. 8. Schematic of biomarker integrated dynamic modelling of $FEV_1$. On the left, the full model space for all CF patients and possible covariates; the large circle is the space for the full dynamic prediction model, and the star denotes the true associates between each CFFPR/EPIC covariate and rapid decline. ON the bottom right, the bottom circle is the space for the external data model that is fit to the CFFPR; the bottom star marks the parameters $\Theta^*$ that would minimize the mathematical distance between the full model with all covariates and the model with only the CFFPR covariates. On the upper right, the circle shows a star being mapped to the same space as the external model, in order to perform model calibration and obtain more efficient, unbiased estimates.

A novel semiparametric "big data" calibration approach (49) may be adapted to examine predictive value of the markers. The approach can be geometrically described (FIG. 8). The algorithm may be programmed using R. Briefly, constrained maximum likelihood estimation may be implemented to fit the Reduced Model described above while accounting for the parameter estimates found from the External Model on the CFF-PR. This estimation, as shown by Chatterjee, produces unbiased estimates with lower standard errors for the Full Model, compared to fitting the Reduced Model alone. The calibrated estimates may be used to determine whether the addition of molecular markers and other EPIC covariates improve prediction of rapid decline.

Figure 9:
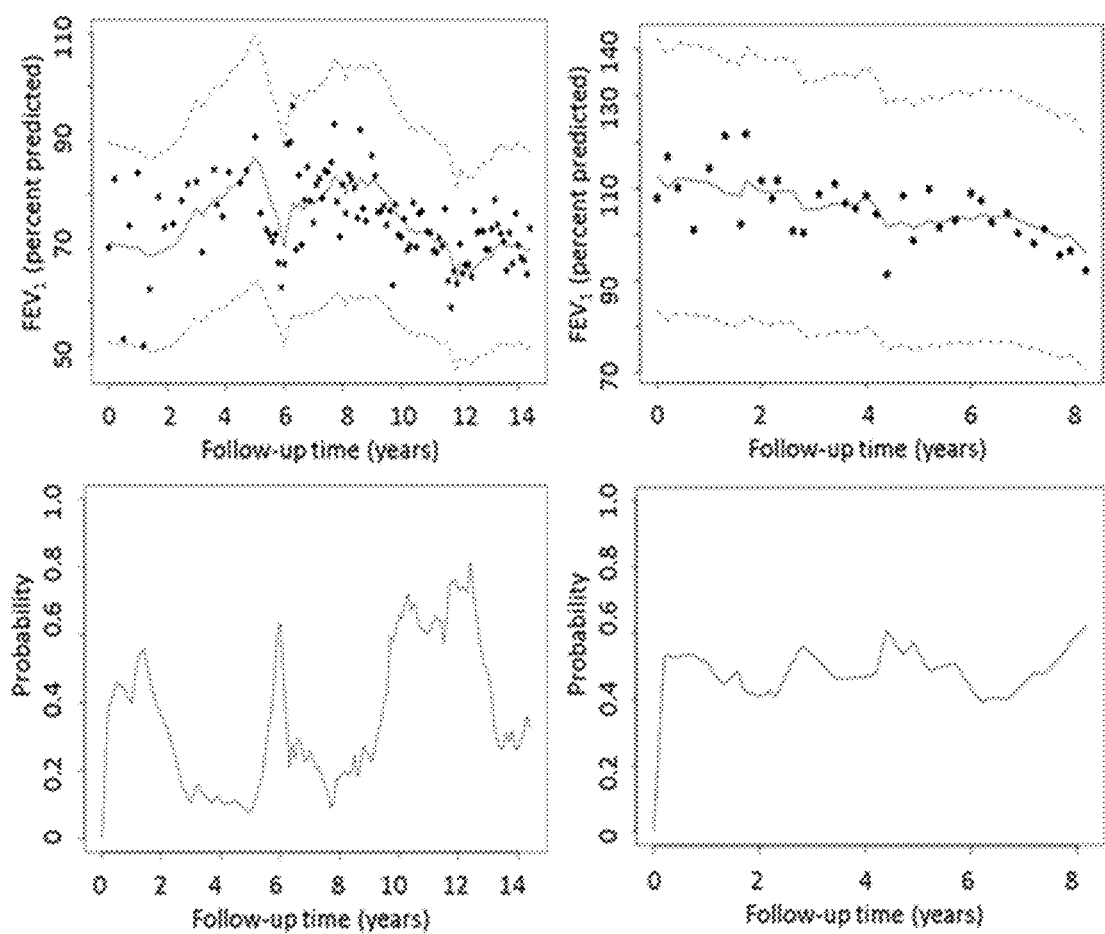
FIG. 9. Dynamic prediction modeling. Dynamic predictions for female (left column) and male (right column) CF patients. In the left column, the female patient had data on 111 encounters in the CFFPR; her age at entry (follow-up time: 0 years on the axis) was 6.1 years. Her decline in $FEV_1$ was highly variable over time (A) with probability of rapid decline on the y-axis in (B); periods of increased risk of rapid decline shown at 16-18 years of age (follow-up time: 10-12 years on the x-axis). By contrast, the male patient (right column) had steadier decline and less availability (C). He had data on 35 encounters in the CFFPR; his age at entry was 14.5 years. He had decreased risk of rapid decline (D), compared to the female patient. Rapid decline was defined as a rate of change in longitudinal $FEV_1$ that fell below 1.5% predicted/year. Threshold was determined as previous reported (53).
Figure 10:
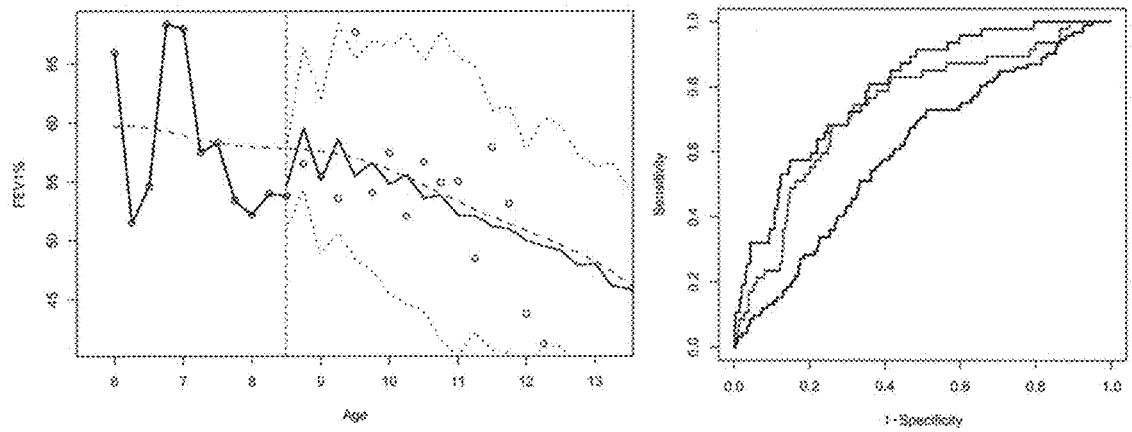
FIG. 10. FEV1 and clinical event forecasting performance. Left panel: the FEV1 forecasting performance for a representative subject from the CFF-PR. Observed FEV1 data (black dots) is fitted with the model (black line) over age; the model was used to predict his subsequent $FEV_1$ data shown after the vertical bar in the plot. To the right of the vertical bar, the solid line and dashed lines are the predicted FEV1 and corresponding 95% confidence bands. The dotted line is the smooth, population-level trajectory for $FEV_1$. Right Panel: the ROC curves for the model fit to PE data. The upper curve is the proposed model, which has the highest AUC (0.74), followed by a model with no subject-level effect and logistic regression (0.68 and 0.61, respectively).

Improved prediction may be assessed by 1) examining the interaction of a given biomarker with age in the Reduced Model; 2) using model diagnostics; 3) fit statistics (e.g., AIC, BIC); 4) the likelihood ratio test to model; an example of the risk function for a patient is in FIG. 9. To validate predictive accuracy, analysis with 20% of the EPIC cohort removed from the modeling may be performed. This subset of the cohort will have covariate data added to the model to check predictive accuracy; metrics here may include mean absolute deviation (MAD) and mean square error (MSE), which have been previously used by Applicant with good success (35).

The predictive value of a subset of proteomic markers is assessed based on the Reduced Model using FD and dynamic prediction as described above. Applicant included the protein similar to dual specificity phosphatase 9, partial as a covariate and its interaction with age in the Reduced Model. Other covariates included in the model were age-specific components to fit the $FEV_1$ trajectory, as shown in the FD analysis in previous studies, and the mild/severe designation from the original study. The proteomic marker was available on 36 EPIC subjects (23 Mild, 13 Severe); these subjects were 6.3 (6.6-7.7) years of age with $FEV_1$ of 95.5 (61-138) % predicted. The median (range) number of PFTs (per subject was 54 (20-93); per-subject follow-up was 11.5 (9.4-12) years. The model showed the proteomic marker was significantly associated with mean $FEV_1$ (coefficient: −8.03, SE: 4.07, z=−2.0, P=0.04) and approached significance in its association with $FEV_1$ decline (coefficient for interaction: 1.03, SE: 0.79, z=1.3, P=0.19). These results suggest that the biomarker has a negative association with overall mean $FEV_1$ but may have a positive effect on rate of $FEV_1$ decline.

Covariate selection may also be performed using Bayesian Ensemble Trees (BET) (50). BET was developed by Applicant as an approach to perform variable selection for modeling $FEV_1$ decline. This approach utilizes the ensemble of classification and regression trees (CART). Each constituent tree is estimated with a subset of similar data, and can be used for covariate selection and imputation of missing data (51). The form of each marker covariate will be modified to examine potential lagged effects on $FEV_1$ decline. For select markers, associations with $FEV_1$ decline can be simultaneously examined using joint models for high-dimensional data (52). To investigate the impact of the collection of markers on rapid decline, PCA may be used to develop composite score(s); the score data may then be included in the model as covariate(s). Alternatively, BET may be used to create step functions representing rapid decline. The step functions can be subsequently smoothed to represent rate of $FEV_1$ decline and construct individual probabilities of rapid decline similar to the dynamic prediction model or risk scores for rapid decline.

The need for analysis of samples collected from subject undergoing modulator therapy is critical, as CFTR modulation has become the standard of care, and this will likely influence the behavior of molecular markers.

Example 1. Improvement of Predicting Lung Function Decline

Figure 11:
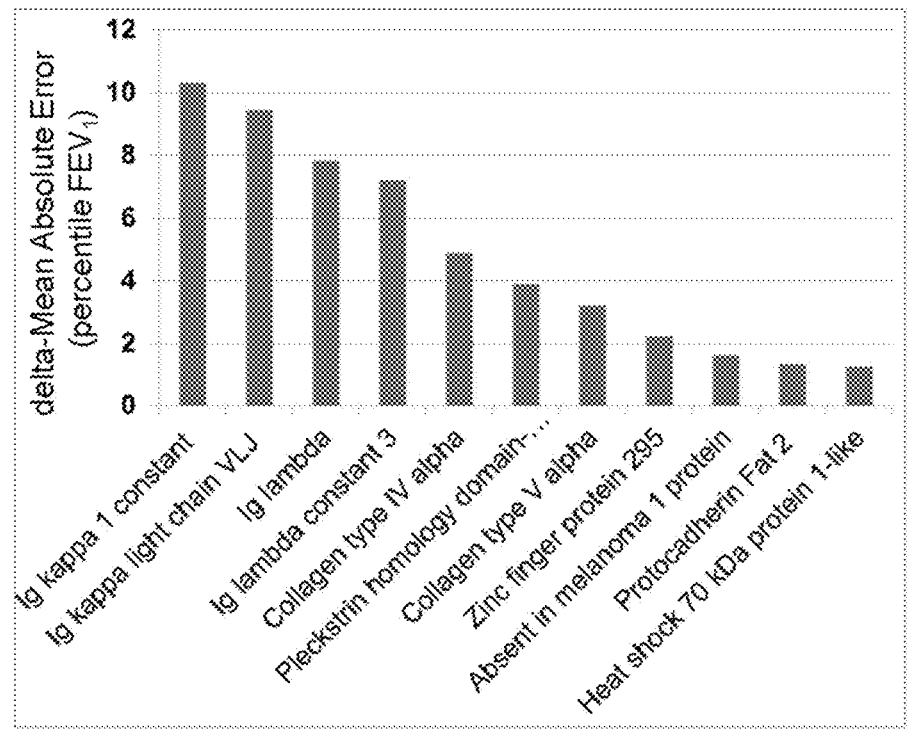
FIG. 11. Marker improvement of FEV1 prediction. Protein markers in serum improve the ability to predict future lung function decline, reducing the error in prediction of absolute FEV1 by up to greater than 10 percentile points.

A number of interventional therapies are used to stave off lung function decline in patients with cystic fibrosis, including antibiotics, anti-inflammatory therapies, hypertonic saline to increase clearance, and others. The largest challenge in CF care is projecting lung function performance and intervening accordingly. Currently, intervention occurs when clear declines in lung function as measured by FEV1 and other lagging indicators are observed. The approach of intervening once lung function has already declined rarely restores lost lung function; therefore, intervening before lung function decline occurs can be beneficial by preventing decline. An example that captures the range of the performance of some of the markers in Table 1 at improving the prediction of lung function is shown in FIG. 11.

Tandem mass spectrometry or ELISA may be used to measure the levels of Ig lambda and Ig kappa chains in collections of blood from a CF patient during their regular hospital visits. The levels of these proteins would be inserted into the algorithm described herein along with the measurements of FEV1 for the patient over a number of hospital visits. The markers can be used individually or in combination. The algorithm will return a score that reflects the risk of lung function decline in the next 18 months. Based on the score returned a physician may choose to be more aggressive with conventional anti-inflammatory therapy to reduce or prevent impeding lung function decline or follow the usual regiment of care if the score does not indicate a high risk of future lung function decline.

Figure 12:
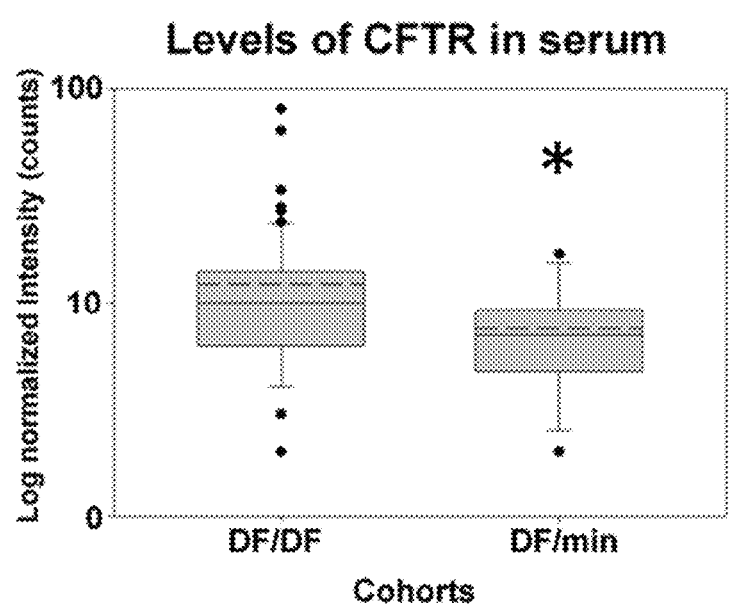
FIG. 12. Quantitation of CFTR by tandem mass spectrometry. Fractionated serum is analyzed for levels of CFTR in homozygote F507del patients versus those with 1 F508del allele with the other allele producing minimal protein. Solid line is median. Dashed line is average. DF/DF average±SEM=12.34±1.44 vs DF/min average±SEV=7.5±1.09. * connotes significant difference, p=0.0092.

Example 2. Measurement of CFTR to Assess the Success of the Delivery of CFTR Gene Therapy A large challenge for gene therapy with the CFTR gene is the lack of effective measures of the delivered CFTR transgene expression. The technology described herein allows us to measure the levels of full length or any portion of CFTR protein. FIG. 12 shows difference measured in the levels of CFTR between patients homozygous for the F508del mutation compared with the levels measured in the serum of patients heterozygous for F508del and various mutations that express minimal levels of protein. The difference observed by the technology claimed here of 1.65-fold reflects the expected higher levels of CFTR expression in the homozygous group. An example of using this technology would be in the context of a CFTR gene therapy trial. In such a trial, measuring the expression of the delivered transgene CFTR would be necessary. The technology described herein may be used to measure level of full length or a portion of CFTR in the serum, plasma, and/or bronchoalveolar lavage to assess the efficiency of gene delivery. An increase in levels of CFTR in serum, for example, would indicate successful delivery of CFTR

REFERENCES

1. Drumm M L, Ziady A G, Davis P B. Genetic variation and clinical heterogeneity in cystic fibrosis. Annu. Rev. Pathol. 2012; 7:267-82
2. Rosenfeld M, VanDevanter D R, Ren C L, Elkin E P, Pasta D J, Konstan M W, Morgan W J, Investigators of Coordinators of the Epidemiologic Study of Cystic Fibrosis. Decline in lung function does not predict future decline in lung function in cystic fibrosis patients. Pediatr Pulmonol 2015 September; 50(9):856-62
3. Szczesniak R D, McPhail G L, Li D, Amin R S, Clancy J P. Predicting future lung function decline in cystic fibrosis patients: Statistical methods and clinical connections. Pediatr Pulmonol 2016 February; 51(2):217-8. PMCID:PMC4770893
4. Accurso F J, Rowe S M, Clancy J P, Boyle M P, Dunitz J M, Durie P R, Sagel S D, Hornick D B, Konstan M W, Donaldson S H, et al. Effect of VX-770 in persons with cystic fibrosis and the G551D-CFTR mutation. N. Engl. J. Med. 2010 Nov. 18; 363(21):1991-2003
5. Wainwright C E, Elborn J S, Ramsey B W, Marigowda G, Huang X, Cipolli M, Colombo C, Davies J C, De B K, Flume P A, et al. Lumacaftor-Ivacaftor in Patients with Cystic Fibrosis Homozygous for Phe508del CFTR. N. Engl. J. Med. 2015 Jul. 16; 373(3):220-31
6. Sanders D B, Bittner R C, Rosenfeld M, Hoffman L R, Redding G J, Goss C H. Failure to recover to baseline pulmonary function after cystic fibrosis pulmonary exacerbation. Am. J. Respir. Crit Care Med. 2010 Sep. 1; 182(5):627-32
7. Chen J, Kinter M, Shank S, Cotton C, Kelley T J, Ziady A G. Dysfunction of Nrf-2 in CF epithelia leads to excess intracellular H2O2 and inflammatory cytokine production. PLoS. One. 2008; 3(10):e3367
8. Ziady A G, Kinter M. Protein sequencing with tandem mass spectrometry. Methods Mol. Biol. 2009; 544:325-41
9. Ziady A G, Sokolow A, Shank S, Corey D, Myers R, Plafker S, Kelley T J. Interaction with CREB binding protein modulates the activities of Nrf2 and NF-kappaB in cystic fibrosis airway epithelial cells. Am. J. Physiol Lung Cell Mol. Physiol 2012 Jun. 1; 302(11):L1221-L1231. PMCID:PMC3379036
10. Chirkova T, Lin S, Oomens A G, Gaston K A, Boyoglu-Barnum S, Meng J, Stobart C C, Cotton C U, Hartert T V, Moore M L, et al. CX3CR1 is an Important Surface Molecule for RSV Infection in Human Airway Epithelial Cells. J. Gen. Virol. 2015 Jun. 25;
11. Sinha C, Zhang W, Moon C S, Actis M, Yarlagadda S, Arora K, Woodroofe K, Clancy J P, Lin S, Ziady A G, et al. Capturing the Direct Binding of CFTR Correctors to CFTR by Using Click Chemistry. Chembiochem. 2015 Jul. 29;
12. Sinha C, Ren A, Arora K, Moon C S, Yarlagadda S, Woodrooffe K, Lin S, Schuetz J D, Ziady A G, Naren A P. PKA and actin play critical roles as downstream effectors in MRP4-mediated regulation of fibroblast migration. Cell Signal. 2015 July; 27(7):1345-55. PMCID: PMC4437852
13. Ziady A G, Heltshe S L, Kelley T J, Muhlebach M S, Accurso F, Pilewski J, Clancy J P, Sagel S D, Joseloff E. Proteomic analyses of serum from CF patients with mild or severe disease reveal the differential expression of proteins that regulate the differentiation of cartilage, myeloid leukocytes, and intestinal epithelia. Pediatr. Pulmonol. Suppl 38, 288. 2014.
14. Sagel S D, Wagner B, Ziady A G, Kelley T J, Muhlebach M S, Accurso F, Pilewski J, Heltshe S L, Clancy J P, Joseloff E. Validation of Candidate Serum Protein and Lipid Markers of Disease Severity In CF. Pediatr. Pulmonol. Suppl 38, 288. 2014.
15. Ziady A G, Lin S, Wyatt C, Clancy J P. Proteomic analyses of BALF reveal potential biomarkers and suggest altered lipid, cyclic nucleotide, and iron metabolism in young CF children versus disease controls. Pediatr. Pulmonol. Suppl 36, 250. 2013.
16. Li Q, Ding X, Thomas J J, Harding C V, Pecora N D, Ziady A G, Shank S, Boom W H, Lancioni C L, Rojas R E. Rv2468c, a novel *Mycobacterium tuberculosis* protein that costimulates human CD4+ T cells through VLA-5. J. Leukoc. Biol. 2012 February; 91(2):311-20. PMCID: PMC3290430
17. Chen X, Shank S, Davis P B, Ziady A G. Nucleolin-mediated cellular trafficking of DNA nanoparticle is lipid raft and microtubule dependent and can be modulated by glucocorticoid. Mol. Ther. 2011 January; 19(1):93-102
18. Tibshirani R J. Regression shrinkage and selection via the lasso. Royal. Statist. Soc B. 1996; 58:267-88
19. Hastie T, Tibshirani R J, Friedman J. The Elements of Statistical Learning: Data Mining, Inference, and Prediction. 2009.
20. Laguna T A, Wagner B D, Luckey H K, Mann S A, Sagel S D, Regelmann W, Accurso F J. Sputum desmosine during hospital admission for pulmonary exacerbation in cystic fibrosis. Chest 2009 December; 136(6):1561-8. PMCID:PMC2789924
21. Nick J A, Sanders L A, Ickes B, Briones N J, Caceres S M, Malcolm K C, Brayshaw S J, Chacon C S, Barboa C M, Jones M C, et al. Blood mRNA biomarkers for detection of treatment response in acute pulmonary exacerbations of cystic fibrosis. Thorax 2013 October; 68(10): 929-37
22. Ratjen F, Saiman L, Mayer-Hamblett N, Lands L C, Kloster M, Thompson V, Emmett P, Marshall B, Accurso F, Sagel S, et al. Effect of azithromycin on systemic markers of inflammation in patients with cystic fibrosis uninfected with *Pseudomonas aeruginosa*. Chest 2012 November; 142(5): 1259-66. PMCID:PMC3610595
23. Sagel S D, Thompson V, Chmiel J F, Montgomery G S, Nasr S Z, Perkett E, Saavedra M T, Slovis B, Anthony M M, Emmett P, et al. Effect of treatment of cystic fibrosis pulmonary exacerbations on systemic inflammation. Ann. Am. Thorac. Soc 2015 May; 12(5):708-17. PMCID: PMC4418340
24. Zemanick E T, Harris J K, Wagner B D, Robertson C E, Sagel S D, Stevens M J, Accurso F J, Laguna T A. Inflammation and airway microbiota during cystic fibrosis pulmonary exacerbations. PLoS. One. 2013; 8(4):e62917. PMCID:PMC3639911
25. Wang X, Venable J, LaPointe P, Hutt D M, Koulov A V, Coppinger J, Gurkan C, Kellner W, Matteson J, Plutner H, et al. Hsp90 cochaperone Aha1 downregulation rescues misfolding of CFTR in cystic fibrosis. Cell 2006 Nov. 17; 127(4):803-15
26. Brebner J A, Stockley R A. Polyclonal free light chains: a biomarker of inflammatory disease or treatment target? F1000. Med. Rep. 2013; 5:4. PMCID:PMC3564472
27. Fischer K, Kettunen J, Wurtz P, Haller T, Havulinna A S, Kangas A J, Soininen P, Esko T, Tammesoo M L, Magi R, et al. Biomarker profiling by nuclear magnetic resonance spectroscopy for the prediction of all-cause mortality: an observational study of 17,345 persons. PLoS. Med. 2014 February; 11(2):e1001606. PMCID: PMC3934819
28. Slobodianik N H, Feliu M S, Perris P, Barbeito S, Strasnoy I, Franchello A, Ferraro M. Inflammatory biomarker profile in children with cystic fibrosis: preliminary study. Proc. Nutr. Soc 2010 August; 69(3):354-6
29. Liou T G, Elkin E P, Pasta D J, Jacobs J R, Konstan M W, Morgan W J, Wagener J S. Year-to-year changes in lung function in individuals with cystic fibrosis. J. Cyst. Fibros. 2010 July; 9(4):250-6. PMCID:PMC4102928
30. Harun S N, Wainwright C, Klein K, Hennig S. A systematic review of studies examining the rate of lung function decline in patients with cystic fibrosis. Paediatr. Respir. Rev. 2016 Mar. 14;
31. Schluchter M D, Konstan M W, Drumm M L, Yankaskas J R, Knowles M R. Classifying severity of cystic fibrosis lung disease using longitudinal pulmonary function data. Am. J. Respir. Crit Care Med. 2006 Oct. 1; 174(7):780-6
32. Ramsay J O, Silverman B W. Functional data analysis. 2nd ed. ed. New York: Springer; 2005. 426 p.

33. Wang J, Xian H, Licis A, Deych E, Ding J, McLeland J, Toedebusch C, Li T, Duntley S, Shannon W. Measuring the impact of apnea and obesity on circadian activity patterns using functional linear modeling of actigraphy data. J. Circadian. Rhythms 2011; 9(1):11. PMCID: PMC3245508
34. Zeitzer J M, David R, Friedman L, Mulin E, Garcia R, Wang J, Yesavage J A, Robert P H, Shannon W. Phenotyping apathy in individuals with Alzheimer disease using functional principal component analysis. Am. J. Geriatr. Psychiatry 2013 April; 21(4):391-7. PMCID: PMC3603283
35. Szczesniak R D, McPhail G L, Duan L L, Macaluso M, Amin R S, Clancy J P. A semiparametric approach to estimate rapid lung function decline in cystic fibrosis. Ann. Epidemiol. 2013 December; 23(12):771-7
36. Taylor-Robinson D, Whitehead M, Diderichsen F, Olesen H V, Pressler T, Smyth R L, Diggle P. Understanding the natural progression in % FEV1 decline in patients with cystic fibrosis: a longitudinal study. Thorax 2012 October; 67(10):860-6. PMCID:PMC3446776
37. Tang Y, Kosorok M R. Developing Adaptive Personalized Therapy for Cystic Fibrosis using Reinforcement Learning. 2012. Report No.: Working Paper 30.
38. Clancy J P, Jain M. Personalized medicine in cystic fibrosis: dawning of a new era. Am. J. Respir. Crit Care Med. 2012 Oct. 1; 186(7):593-7
39. James G M, Hastie T J, Sugar C A. Principal component models for sparse functional data. Biometrika 2000; 87(3):587-602
40. Diggle P J, Sousa I, Asar O. Real-time monitoring of progression towards renal failure in primary care patients. Biostatistics. 2015 July; 16(3):522-36
41. La Rosa P S, Brooks J P, Deych E, Boone E L, Edwards D J, Wang Q, Sodergren E, Weinstock G, Shannon W D. Hypothesis testing and power calculations for taxonomic-based human microbiome data. PLoS. One. 2012; 7(12): e52078. PMCID:PMC3527355
42. Lancioni C L, Li Q, Thomas J J, Ding X, Thiel B, Drage M G, Pecora N D, Ziady A G, Shank S, Harding C V, et al. *Mycobacterium tuberculosis* lipoproteins directly regulate human memory CD4(+) T cell activation via Toll-like receptors 1 and 2. Infect. Immun. 2011 February; 79(2):663-73
43. Yanagisawa K, Shyr Y, Xu B J, Massion P P, Larsen P H, White B C, Roberts J R, Edgerton M, Gonzalez A, Nadaf S, et al. Proteomic patterns of tumour subsets in non-small-cell lung cancer. Lancet 2003 Aug. 9; 362 (9382):433-9
44. Kim P Y, Tan O, Diakiw S M, Carter D, Sekerye E O, Wasinger V C, Liu T, Kavallaris M, Norris M D, Haber M, et al. Identification of plasma complement C3 as a potential biomarker for neuroblastoma using a quantitative proteomic approach. J. Proteomics. 2014 Jan. 16; 96:1-12
45. Tucholska M, Bowden P, Jacks K, Zhu P, Furesz S, Dumbrovsky M, Marshall J. Human serum proteins fractionated by preparative partition chromatography prior to LC-ESI-MS/MS. J. Proteome. Res. 2009 March; 8(3): 1143-55
46. Chmiel J, Ziady A, Cantin A M, Comhair S, Hazen S L, Schluchter M, Margevicius C, Bucur P, Campbell P W, III, Konstan M. The effect of sulforaphane in broccoli sprouts on Nrf2 activation, glutathione, markers of oxidative stress, and neutrophil migration. Pediatr. Pulmonol. Suppl 35, 250. 2012.
47. Rosenfeld M, Emerson J, McNamara S, Joubran K, Retsch-Bogart G, Graff G R, Gutierrez H H, Kanga J F, Lahiri T, Noyes B, et al. Baseline characteristics and factors associated with nutritional and pulmonary status at enrollment in the cystic fibrosis EPIC observational cohort. Pediatr. Pulmonol. 2010 September; 45(9):934-44
48. Asar O, Ilk O. mmm: an R package for analyzing multivariate longitudinal data with multivariate marginal models. Comput. Methods Programs Biomed. 2013 December; 112(3):649-54
49. Chatterjee N, Chen Y H, Maas P, Carroll R J. Constrained Maximum Likelihood Estimation for Model Calibration Using Summary-level Information from External Big Data Sources. J. Am. Stat. Assoc. 2016 March; 111(513):107-17. PMCID:PMC4994914
50. Duan L L, Clancy J P, Szczesniak R D. Bayesian Ensemble Trees (BET) for Clustering and Prediction in Heterogeneous Data. J. Comput. Graph. Stat. 2016; 25(3): 748-61. PMCID:PMC4980076
51. Chipman H A, George E L, McCulloch R E. Bart: Bayesian Additive Regression Trees. Ann Appl Stat 2014; 23(1):42-59
52. Verbeke G, Fieuws S, Molenberghs G, Davidian M. The analysis of multivariate longitudinal data: a review. Stat. Methods Med. Res. 2014 February; 23(1):42-59. PMCID: PMC3404254
53. Fieuws S, Verbeke G, Molenberghs G. Random-effects models for multivariate repeated measures. Stat Methods Med. Res. 2007 October; 16(5):387-97
54. Albert P S, Shih J H. A N APPROACH FOR JOINTLY MODELING MULTIVARIATE LONGITUDINAL MEASUREMENTS AND DISCRETE TIME-TO-EVENT DATA. Ann Appl Stat 2010 Sep. 1; 4(3):1517-32. PMCID:PMC3175771
55. Duan L L, Clancy J P, Szczesniak R D. Joint Hierarchical Gaussian Process Model with Application to Forecast in Medical Monitoring 2014 Jan. 8; eprint arXiv: 1408.4660.
56. Obuchowski N A, McClish D K. Sample size determination for diagnostic accuracy studies involving binormal ROC curve indices. Stat Med. 1997 Jul. 15; 16(13):1529-42
57. Fieuws S, Verbeke G, Maes B, Vanrenterghem Y. Predicting renal graft failure using multivariate longitudinal profiles. Biostatistics. 2008 July; 9(3):419-31
58. Diggle, P. J., Sousa, I., Asar, O. (2015). Real-time monitoring of progression to-wards renal failure in primary care patients. Biostatistics, 16(3): 522-36. DOI: 10.1093/biostatistics/kxu053.

Jiang, C.-R., Wang, J.-L. (2010). Covariate-adjusted functional principal components analysis for longitudinal data. The Annals of Statistics, 38(2): 1194-1226.

59. Szczesniak, R., McPhail, G. L., Duan, L. L., Macaluso, M., Amin, R. S., Clancy, J. P. (2013). A semiparametric approach to estimate rapid lung function decline in cystic fibrosis. Annals of Epidemiology, 23(12): 771-7. DOI: 10.1016/j.annepidem.2013.08.009. PMID: 24103586.,
60. Szczesniak, R., Li, D., Su, W., Pestian, J., Seid, M., Clancy, J. P. (2017). Pheno-types of Rapid Cystic Fibrosis Lung Disease Progression during Adolescence and Young Adulthood. American Journal of Respiratory and Critical Care Medicine, 196(4): 471-478. DOI: 10.1164/rccm.201612-25740C. PMID: 28410569
61. Yao, F., Muller, H.-G., Wang, J.-L. (2005). Functional Data Analysis for Sparse Longitudinal Data. Journal of the American Statistical Association, 100(470): DOI: 10.1198/016214504000001745.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A treatment method comprising:
   a. detecting expression of each protein of a protein set in a sample from an individual diagnosed with cystic fibrosis (CF), wherein said protein set comprises one or more proteins selected from glutamate receptor 2, uridine-cytidine kinase-like 1, chromosome 12 ORF 42, or keratin 18 (KRT18);
   b. obtaining a risk probability score based on the expression level of said protein set of step a; and
   c. treating said individual with one or both of an anti-inflammatory and an anti-bacterial based on said risk probability score.

2. The method of claim 1, wherein said risk probability score is predictive of one or more clinical outcomes in said individual.

3. The method of claim 2, wherein said one or more clinical outcomes is selected from lung function decline as measured by Forced Expiratory Volume in 1 sec ($FEV_1$), rate of change of $FEV_1$, probability of rapid decline, risk of pulmonary exacerbation, body mass index (BMI), pulmonary exacerbation (PE), or combinations thereof.

4. The method of claim 1, wherein said sample is selected from blood, serum, urine, plasma, peripheral blood mononuclear cell (PBMC), bronchoalveolar lavage fluid (BALF), nasal and/or lower airway brushings, sputum, GI biopsies, lung explants, or combinations thereof.

5. The method of claim 1 wherein said detecting step is carried out using mass spectrometry.

6. The method of claim 1, wherein said detecting step is carried out via one or both of ELISA and mass spectrometry.

7. The method of claim 1 wherein said risk probability score is calculated using a computer.

8. A treatment method comprising
   a. calculating a risk probability score from expression levels of a protein set from a sample obtained from an individual diagnosed with Cystic Fibrosis, wherein said protein set comprises one or more proteins selected from glutamate receptor 2, uridine-cytidine kinase-like 1, chromosome 12 ORF 42, or keratin 18 (KRT18); and
   b. forecasting lung function trajectory based on said risk probability score; and
   c. treating said individual with one or both of an anti-inflammatory and an anti-bacterial based on said risk probability score;
wherein one or both of step (a) and step (b) are performed on a computer.

9. The method of claim 8, wherein said biomarker expression levels are obtained via mass spectrometry.

10. The method of claim 2, wherein said clinical outcome is rate of change in FEV1.

11. The method of claim 1, further comprising the determining one or more inputs selected from Forced Expiratory Volume in 1 sec ($FEV_1$), body mass index (BMI), pulmonary exacerbations (PE), age, gender, sex, genotype, respiratory infection status, birth year, a mutation at position 508 of the gene for cystic fibrosis transmembrane conductance regulator (CFTR), a mutation at position 507 of the gene for cystic fibrosis transmembrane conductance regulator (CFTR), any mutation the gene for cystic fibrosis transmembrane conductance regulator (CFTR), baseline FEV1, Cystic Fibrosis (CF)-related diabetes, number of follow-up visits for said individual, number of hospitalizations for said individual, use of state-sponsored insurance by said individual, or antibiotic status in said individual, wherein said one or more inputs is used to calculate said risk probability score.

12. The method of claim 11, wherein said respiratory infection status is selected from *P. aeruginosa* infection status, *S. maltophilia* infection status, Methicillin-resistant *Staphylococcus aureus* (MRSA) infection status, or combinations thereof.

13. The method of claim 8, wherein said risk probability score further includes use of an input selected from Forced Expiratory Volume in 1 sec ($FEV_1$), body mass index (BMI), pulmonary exacerbations (PE), age, gender, sex, genotype, respiratory infection status, birth year, a mutation at position 508 of the gene for cystic fibrosis transmembrane conductance regulator (CFTR), a mutation at position 507 of the gene for cystic fibrosis transmembrane conductance regulator (CFTR), any mutation the gene for cystic fibrosis transmembrane conductance regulator (CFTR), wherein said input is used to calculate said risk probability score.

14. The method of claim 13, wherein said respiratory infection status is selected from *P. aeruginosa* infection status, *S. maltophilia* infection status, Methicillin-resistant *Staphylococcus aureus* (MRSA) infection status, or combinations thereof.

15. The method of claim 8, within said treatment method employs a computer, and wherein said computer comprises a graphical user interface (GUI) configured to allow an end user to interactively explore said predictive model within a web browser.

\* \* \* \* \*